(12) United States Patent
Kshirsagar et al.

(10) Patent No.: US 8,158,794 B2
(45) Date of Patent: Apr. 17, 2012

(54) HYDROXYALKYL SUBSTITUTED IMIDAZOQUINOLINE COMPOUNDS AND METHODS

(75) Inventors: Tushar A. Kshirsagar, Woodbury, MN (US); Bryon A. Merrill, River Falls, WI (US); Shri Niwas, Maple Grove, MN (US); Gregory D. Lundquist, Jr., Eagan, MN (US); Philip D. Heppner, Forest Lake, MN (US); Michael E. Danielson, Saint Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 912 days.

(21) Appl. No.: 11/885,006

(22) PCT Filed: Feb. 22, 2006

(86) PCT No.: PCT/US2006/006042
§ 371 (c)(1),
(2), (4) Date: Aug. 18, 2008

(87) PCT Pub. No.: WO2006/091567
PCT Pub. Date: Aug. 31, 2006

(65) Prior Publication Data
US 2009/0069314 A1     Mar. 12, 2009

Related U.S. Application Data

(60) Provisional application No. 60/655,495, filed on Feb. 23, 2005.

(51) Int. Cl.
C07D 471/00     (2006.01)
A61K 31/535    (2006.01)
(52) U.S. Cl. ........................... 546/82; 514/222.8
(58) Field of Classification Search ............ None
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,605,899 A | 2/1997 | Gerster et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |
| 6,465,654 B2 | 10/2002 | Gerster et al. |
| 6,486,168 B1 | 11/2002 | Skwierczynski et al. |
| 6,514,985 B1 | 2/2003 | Gerster et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |

(Continued)

FOREIGN PATENT DOCUMENTS

EP     0 394 026     10/1990

(Continued)

OTHER PUBLICATIONS

Yutilov et al., Synthesis and some reactions of 4-nitroimidazo[4-5-c]pyridin-2-ones. VINITI.1978:1193-78. Russian. CAPLUS English Abstract DN 91:175261.

Wozniak et al., "The Animation of 3-nitro-1, 5-naphthyridines by Liquid Ammonia/Potassium Permanganate[1,2]. A New and Convenient Animation Method.", *Journal of the Royal Netherlands Chemical Society*, 102, pp. 511-513, Dec. 12, 1983.

Brennan et al., "Automated Bioassay of Interferons in Micro-test Plates.", *Biotechniques*, June/July, 78, 1983.

Testerman et al., "Cytokine Induction by the Immunomodulators Imiquimod and S-27609.", *Journal of Leukocyte Biology*, vol. 58, pp. 365-372, Sep. 1995.

(Continued)

*Primary Examiner* — Janet Andres
*Assistant Examiner* — Heidi Reese

(57) ABSTRACT

Certain imidazoquinolines with a hydroxymethyl or hydroxyethyl substituent at the 2-position, and an aryl or heteroaryl substituent at the 7-position, pharmaceutical compositions containing the compounds, intermediates, methods of making and methods of use of these compounds as immunomodulators, for preferentially inducing IFN-α biosynthesis in animals and in the treatment of diseases including viral and neoplastic diseases are disclosed.

18 Claims, 1 Drawing Sheet

U.S. PATENT DOCUMENTS

| | | |
|---|---|---|
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,809,203 B2 | 10/2004 | Gerster et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,878,719 B2 | 4/2005 | Lindstrom et al. |
| 6,888,000 B2 | 5/2005 | Crooks et al. |
| 6,894,060 B2 | 5/2005 | Slade |
| 6,897,221 B2 | 5/2005 | Crooks et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,225 B2 | 9/2005 | Lee et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,523 B2 | 7/2006 | Crooks et al. |
| 7,091,214 B2 * | 8/2006 | Hays et al. ............. 514/293 |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,132,438 B2 | 11/2006 | Frenkel et al. |
| 7,148,232 B2 | 12/2006 | Gerster et al. |
| 7,157,453 B2 | 1/2007 | Crooks et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,301,027 B2 | 11/2007 | Colombo et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,485,432 B2 | 2/2009 | Fink et al. |
| 7,544,697 B2 | 6/2009 | Hays et al. |
| 7,576,068 B2 | 8/2009 | Averett |
| 7,578,170 B2 | 8/2009 | Mayer et al. |
| 7,579,359 B2 | 8/2009 | Krepski et al. |
| 7,598,382 B2 * | 10/2009 | Hays et al. ............. 546/82 |
| 7,612,083 B2 | 11/2009 | Griesgraber |
| 7,648,997 B2 | 1/2010 | Kshirsagar et al. |
| 7,655,672 B2 | 2/2010 | Statham et al. |
| 7,687,628 B2 | 3/2010 | Gutman et al. |
| 7,696,159 B2 | 4/2010 | Owens et al. |
| 7,699,057 B2 | 4/2010 | Miller et al. |
| 7,731,967 B2 | 6/2010 | O'Hagan et al. |
| 7,799,800 B2 | 9/2010 | Wightman |
| 7,879,849 B2 | 2/2011 | Hays et al. |
| 7,884,207 B2 | 2/2011 | Stoermer et al. |
| 7,888,349 B2 | 2/2011 | Kshirsagar et al. |
| 7,897,597 B2 | 3/2011 | Lindstrom et al. |
| 7,897,609 B2 | 3/2011 | Niwas et al. |
| 7,897,767 B2 | 3/2011 | Kshirsagar et al. |
| 7,902,209 B2 | 3/2011 | Statham et al. |
| 7,902,210 B2 | 3/2011 | Statham et al. |
| 7,902,211 B2 | 3/2011 | Statham et al. |
| 7,902,212 B2 | 3/2011 | Statham et al. |
| 7,902,213 B2 | 3/2011 | Statham et al. |
| 7,902,214 B2 | 3/2011 | Statham et al. |
| 7,902,215 B2 | 3/2011 | Statham et al. |
| 7,902,216 B2 | 3/2011 | Statham et al. |
| 7,902,242 B2 | 3/2011 | Statham et al. |
| 7,902,243 B2 | 3/2011 | Statham et al. |
| 7,902,244 B2 | 3/2011 | Statham et al. |
| 7,902,245 B2 | 3/2011 | Statham et al. |
| 7,902,246 B2 | 3/2011 | Statham et al. |
| 7,968,562 B2 | 6/2011 | Skwierczynski et al. |
| 7,968,563 B2 | 6/2011 | Kshirsagar et al. |
| 7,993,659 B2 | 8/2011 | Noelle et al. |
| 8,017,779 B2 | 9/2011 | Merrill et al. |
| 8,026,366 B2 | 9/2011 | Prince et al. |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2003/0133913 A1 | 7/2003 | Tomai et al. |
| 2003/0139364 A1 | 7/2003 | Krieg et al. |
| 2004/0014779 A1 | 1/2004 | Gorden et al. |
| 2004/0132079 A1 | 7/2004 | Gupta et al. |
| 2004/0175336 A1 | 9/2004 | Egging et al. |
| 2004/0180919 A1 | 9/2004 | Lee et al. |
| 2004/0191833 A1 | 9/2004 | Fink et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0048072 A1 | 3/2005 | Kedl et al. |
| 2005/0059072 A1 | 3/2005 | Birmachu et al. |
| 2005/0070460 A1 | 3/2005 | Hammerbeck et al. |
| 2005/0096259 A1 | 5/2005 | Tomai et al. |
| 2005/0106300 A1 | 5/2005 | Chen et al. |
| 2005/0158325 A1 | 7/2005 | Hammerbeck et al. |
| 2005/0165043 A1 | 7/2005 | Miller et al. |
| 2005/0171072 A1 | 8/2005 | Tomai et al. |
| 2005/0239735 A1 | 10/2005 | Miller et al. |
| 2005/0245562 A1 | 11/2005 | Garcia-Echeverria et al. |
| 2006/0045885 A1 | 3/2006 | Kedl et al. |
| 2006/0045886 A1 | 3/2006 | Kedl |
| 2006/0051374 A1 | 3/2006 | Miller et al. |
| 2006/0088542 A1 | 4/2006 | Braun |
| 2006/0142202 A1 | 6/2006 | Alkan et al. |
| 2006/0142235 A1 | 6/2006 | Miller et al. |
| 2006/0195067 A1 | 8/2006 | Wolter et al. |
| 2006/0216333 A1 | 9/2006 | Miller et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0123559 A1 | 5/2007 | Statham et al. |
| 2007/0155767 A1 | 7/2007 | Radmer et al. |
| 2007/0166384 A1 | 7/2007 | Zarraga et al. |
| 2007/0167479 A1 | 7/2007 | Busch et al. |
| 2007/0213355 A1 | 9/2007 | Capraro et al. |

| | | |
|---|---|---|
| 2007/0219196 A1 | 9/2007 | Krepski et al. |
| 2007/0243215 A1 | 10/2007 | Miller et al. |
| 2007/0259881 A1 | 11/2007 | Dellaria et al. |
| 2007/0259907 A1 | 11/2007 | Prince |
| 2007/0287725 A1 | 12/2007 | Moser et al. |
| 2007/0292456 A1 | 12/2007 | Hammerbeck et al. |
| 2008/0015184 A1 | 1/2008 | Kshirsagar et al. |
| 2008/0039533 A1 | 2/2008 | Sahouani et al. |
| 2008/0063714 A1 | 3/2008 | Sahouani et al. |
| 2008/0070907 A1 | 3/2008 | Griesgraber et al. |
| 2008/0085895 A1 | 4/2008 | Griesgraber et al. |
| 2008/0119508 A1 | 5/2008 | Slade et al. |
| 2008/0188513 A1 | 8/2008 | Skwierczynski et al. |
| 2008/0193468 A1 | 8/2008 | Levy et al. |
| 2008/0193474 A1 | 8/2008 | Griesgraber et al. |
| 2008/0207674 A1 | 8/2008 | Stoesz et al. |
| 2008/0213308 A1 | 9/2008 | Valiante et al. |
| 2008/0262021 A1 | 10/2008 | Capraro et al. |
| 2008/0262022 A1 | 10/2008 | Lee et al. |
| 2008/0269192 A1 | 10/2008 | Griesgraber et al. |
| 2008/0306252 A1 | 12/2008 | Crooks et al. |
| 2008/0306266 A1 | 12/2008 | Martin et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0023720 A1 | 1/2009 | Kshirsagar et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0035323 A1 | 2/2009 | Stoermer et al. |
| 2009/0062272 A1 | 3/2009 | Bonk et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0124652 A1 | 5/2009 | Ach et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0202443 A1 | 8/2009 | Miller et al. |
| 2009/0221551 A1 | 9/2009 | Kshirsagar et al. |
| 2009/0221556 A1 | 9/2009 | Kshirsagar et al. |
| 2009/0240055 A1 | 9/2009 | Krepski et al. |
| 2009/0246174 A1 | 10/2009 | Rook et al. |
| 2009/0253695 A1 | 10/2009 | Kshirsagar et al. |
| 2009/0270443 A1 | 10/2009 | Stoermer et al. |
| 2009/0298821 A1 | 12/2009 | Kshirsagar et al. |
| 2009/0306388 A1 | 12/2009 | Zimmerman et al. |
| 2010/0028381 A1 | 2/2010 | Gorski et al. |
| 2010/0056557 A1 | 3/2010 | Benninghoff et al. |
| 2010/0096287 A1 | 4/2010 | Stoesz et al. |
| 2010/0113565 A1 | 5/2010 | Gorden et al. |
| 2010/0152230 A1 | 6/2010 | Dellaria et al. |
| 2010/0158928 A1 | 6/2010 | Stoermer et al. |
| 2010/0173906 A1 | 7/2010 | Griesgraber |
| 2010/0180902 A1 | 7/2010 | Miller et al. |
| 2010/0240693 A1 | 9/2010 | Lundquist et al. |

FOREIGN PATENT DOCUMENTS

| | | |
|---|---|---|
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 92/15581 A1 | 9/1992 |
| WO | WO 92/15582 A1 | 9/1992 |
| WO | WO 02/36592 | 5/2002 |
| WO | WO 03/009852 A1 | 2/2003 |
| WO | WO 2006/028451 | 3/2006 |
| WO | WO 2006/063072 | 6/2006 |
| WO | WO 2006/121528 | 11/2006 |
| WO | WO 2007/030775 | 3/2007 |

OTHER PUBLICATIONS

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Development of a Topically Active Imiquimod Formulation.", *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Biorganic & Medicinal Chemistry*, 11, pp. 2541-2550 (2003).

\* cited by examiner

HYDROXYALKYL SUBSTITUTED IMIDAZOQUINOLINE COMPOUNDS AND METHODS

CROSS-REFERENCE TO RELATED APPLICATIONS

This application is a national stage filing under 35 U.S.C. §371 of PCT International application PCT/US2006/006042 designating the United States of America, and filed Feb. 22, 2006. This application claims the benefit under 35 U.S.C. §119 of U.S. provisional application Ser. No. 60/655,495, filed Feb. 23, 2005.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY

The present invention provides a new class of compounds which preferentially induce the biosynthesis of interferon (α) (IFN-α) in animals. Such compounds are of the following Formulas I, II, and III:

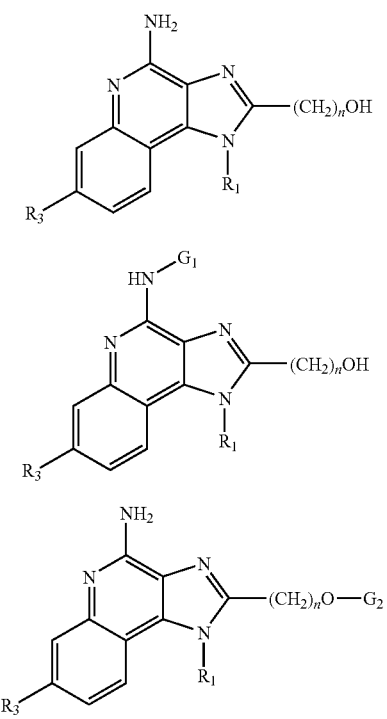

wherein $R_1$, $R_3$, $G_1$, $G_2$, and n are as defined below.

It has now surprisingly been discovered that the amount of TNF-α induced by the 2-(hydroxyalkyl) substituted compounds of the invention is substantially less than the amount of TNF-α induced by closely related analogs having an alkyl or alkyl ether substituent at the 2-position and that the compounds of the invention still retain the ability to induce the biosynthesis of IFN-α. See, for example, FIGS. 1 and 2 below. The reduction in the amount of TNF-α induced is seen over a broad range of test concentrations. In some embodiments the amount of TNF-α induced by the compounds of the invention is at least two-fold less than the amount of TNF-α induced by analogs having an alkyl or alkyl ether substituent at the 2-position. In other embodiments the amount of TNF-α induced by the compounds of the invention is at least three-fold less than the amount of TNF-α induced by analogs having an alkyl or alkyl ether substituent at the 2-position. In still other embodiments the amount of TNF-α induced by the compounds of the invention is at least four-fold less than the amount of TNF-α induced by analogs having an alkyl or alkyl ether substituent at the 2-position.

As used herein "substantially less than the amount of TNF-α" means that there is at least a two-fold reduction in the maximal TNF-α response as determined using the test methods described herein.

The compounds or salts of Formulas I, II, and III are especially useful as immune response modifiers due to their ability to preferentially induce interferon-α, thus providing a benefit over compounds that also induce pro-inflammatory cytokines (e.g. TNF-α) or that induce pro-inflammatory cytokines at higher levels.

A compound is said to preferentially induce IFN-α if, when tested according to the test methods described herein, the effective minimum concentration for IFN-α induction is less than the effective minimum concentration for TNF-α induction. In some embodiments, the effective minimum concentration for IFN-α induction is at least 3-fold less than the effective minimum concentration for TNF-α induction. In some embodiments, the effective minimum concentration for IFN-α induction is at least 6-fold less than the effective minimum concentration for TNF-α induction. In other embodiments, the effective minimum concentration for IFN-α induction is at least 9-fold less than the effective minimum concentration for TNF-α induction. In some embodiments, when tested according to the test methods described herein, the amount TNF-α induced by compounds of the invention is at or below the background level of TNF-α in the test method.

The invention further provides pharmaceutical compositions containing an effective amount of a compound or salt of Formulas I, II, and/or III and methods of preferentially inducing the biosynthesis of IFN-α in an animal, and treating a viral infection or disease and/or treating a neoplastic disease in an animal by administering an effective amount of a compound or salt of Formulas I, II, and/or III or a pharmaceutical compositions containing an effective amount of a compound or salt of Formulas I, II, and/or III to the animal.

In addition, methods of synthesizing compounds of Formulas I, II, and III and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

Figure 1:
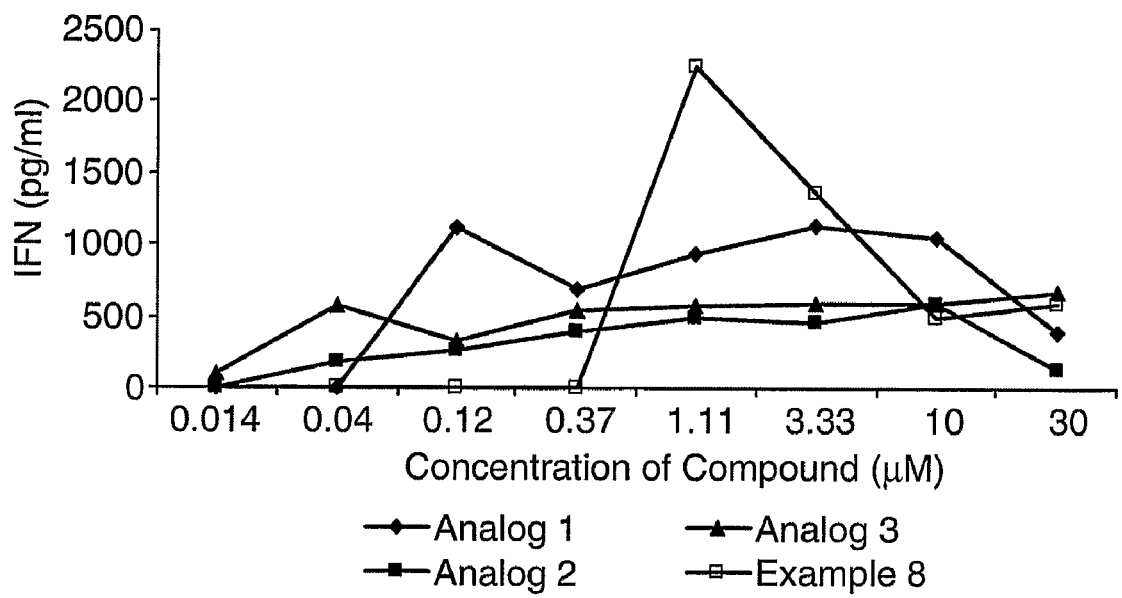
FIG. 1 shows the IFN-α dose response curves (corresponding to values shown in Table 3 below) for Example 8, Analog 1, Analog 2, and Analog 3.

The present invention provides compounds of the following Formulas I, II, and III:

[Structure I: 4-amino imidazoquinoline with $R_3$, $R_1$, and $(CH_2)_n OH$ substituents]

[Structure II: with $HN-G_1$, $R_3$, $R_1$, and $(CH_2)_n OH$ substituents]

[Structure III: with $NH_2$, $R_3$, $R_1$, and $(CH_2)_n O-G_2$ substituents]

wherein $R_1$, $R_3$, $G_1$, $G_2$, and n are as defined below; and pharmaceutically acceptable salts thereof.

In one embodiment, the present invention provides a compound of the following Formula I:

[Structure I]

wherein:

n is 1 or 2;

$R_1$ is selected from the group consisting of:
—$R_4$,
—X—$R_4$,
—X—Y—$R_4$, and
—X—$R_5$;

$R_3$ is selected from the group consisting of:
—Z—Ar,
—Z—Ar'-Y—$R_4$, and
—Z—Ar'-X—Y—$R_4$;

Ar is selected from the group consisting of aryl and heteroaryl both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, amino, alkylamino, and dialkylamino;

X is alkylene optionally interrupted by one —O— group;

Y is selected from the group consisting of:
—O—,
—C($R_6$)—,
—C($R_6$)—N($R_8$)—,
—S(O)$_{0-2}$—,
—N($R_8$)-Q-,

[ring structures containing N—Q, N—$R_7$—N—Q, $R_{10}$, and N—C($R_6$)—N ring groups], and Z is selected from the group consisting of a bond and alkylene;

$R_4$ is selected from the group consisting of hydrogen, alkyl, alkenyl, aryl, arylalkylenyl, heteroaryl, heteroarylalkylenyl, and heterocyclyl, wherein the alkyl, alkenyl, aryl, arylalkylenyl, heteroaryl, heteroarylalkylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and, in the case of alkyl, alkenyl, and heterocyclyl, oxo;

$R_5$ is selected from the group consisting of:

[ring/group structures: —N($R_7$)—C($R_6$), —N($R_7$)—S(O)$_2$, —N($R_8$)—C($R_6$)—N with (CH$_2$)$_a$/(CH$_2$)$_b$ and A, and $R_{10}$ ring with N—C($R_6$)—N with (CH$_2$)$_a$/(CH$_2$)$_b$ and A];

$R_6$ is selected from the group consisting of =O and =S;

$R_7$ is $C_{2-7}$ alkylene;

$R_8$ is selected from the group consisting of hydrogen, alkyl, alkoxyalkylenyl, hydroxyalkylenyl, arylalkylenyl, and heteroarylalkylenyl;

$R_{10}$ is $C_{3-8}$ alkylene;

A is selected from the group consisting of —O—, —C(O)—, —CH$_2$—, —S(O)$_{0-2}$—, and —N(Q-R$_4$)—;

Q is selected from the group consisting of a bond, —C(R$_6$)—, —S(O)$_2$, —C(R$_6$)—N(R$_8$)—, —S(O)$_2$—N(R$_8$)—, —C(R$_6$)—O—, and —C(R$_6$)—S—; and a and b are independently integers from 1 to 6 with the proviso that a+b is ≦7;

or a pharmaceutically acceptable salt thereof.

In another embodiment, the present invention provides a compound of the following Formula II, which is a prodrug:

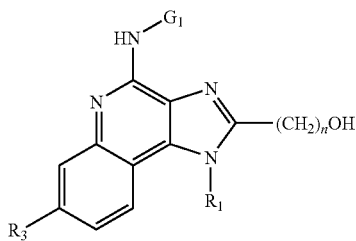

II wherein:

$G_1$ is selected from the group consisting of:
—C(O)—R',
α-aminoacyl,
α-aminoacyl-α-aminoacyl,
—C(O)—O—R',
—C(O)—N(R")R',
—C(=NY')—R',
—CH(OH)—C(O)—OY',
—CH(OC$_{1-4}$ alkyl)Y$_0$,
—CH$_2$Y$_1$, and
—CH(CH$_3$)Y$_1$;

R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;

α-aminoacyl is an α-aminoacyl group derived from an α-amino acid selected from the group consisting of racemic, D-, and L-amino acids;

Y' is selected from the group consisting of hydrogen, $C_{1-6}$ alkyl, and benzyl;

Y$_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-16}$ alkylamino-$C_{1-4}$ alkylenyl;

Y$_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl;

n is 1 or 2;

$R_1$ is selected from the group consisting of:
—R$_4$,
—X—R$_4$,
—X—Y—R$_4$, and
—X—R$_5$;

$R_3$ is selected from the group consisting of:
—Z—Ar,
—Z—Ar'-Y—R$_4$, and
—Z—Ar'-X—Y—R$_4$;

Ar is selected from the group consisting of aryl and heteroaryl both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, amino, alkylamino, and dialkylamino;

X is alkylene optionally interrupted by one —O— group;

Y is selected from the group consisting of:
—O—,
—C(R$_6$)—,
—C(R$_6$)—N(R$_8$)—,
—S(O)$_{0-2}$—,
—N(R$_8$)-Q-,

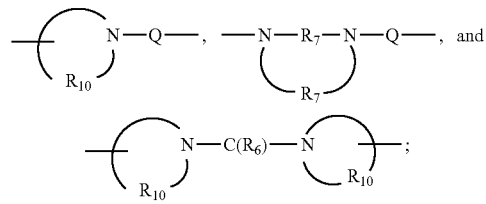

Z is selected from the group consisting of a bond and alkylene;

$R_4$ is selected from the group consisting of hydrogen, alkyl, alkenyl, aryl, arylalkylenyl, heteroaryl, heteroarylalkylenyl, and heterocyclyl, wherein the alkyl, alkenyl, aryl, arylalkylenyl, heteroaryl, heteroarylalkylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and, in the case of alkyl, alkenyl, and heterocyclyl, oxo;

$R_5$ is selected from the group consisting of:

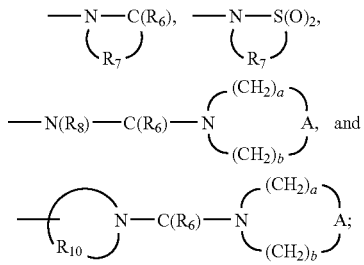

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_{10}$ is $C_{3-8}$ alkylene;
A is selected from the group consisting of —O—, —C(O)—, —CH$_2$—, —S(O)$_{0-2}$—, and —N(Q-R$_4$)—;
Q is selected from the group consisting of a bond, —C(R$_6$)—, —S(O)$_2$, —C(R$_6$)—N(R$_8$)—, —S(O)$_2$—N(R$_8$)—, —C(R$_6$)—O—, and —C(R$_6$)—S—; and
a and b are independently integers from 1 to 6 with the proviso that a+b is ≦7;
or a pharmaceutically acceptable salt thereof.

In another embodiment, the present invention provides a compound of the following Formula III, which is a prodrug:

wherein:
G$_2$ is selected from the group consisting of:
—X$_2$—C(O)—R',
α-aminoacyl,
α-aminoacyl-α-aminoacyl,
—X$_2$—C(O)—O—R', and
—C(O)—N(R")R';
X$_2$ is selected from the group consisting of a bond; —CH$_2$—O—; —CH(CH$_3$)—O—; —C(CH$_3$)$_2$—O—; and, in the case of —X$_2$—C(O)—O—R', —CH$_2$—NH—;
R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;
α-aminoacyl is an α-aminoacyl group derived from an α-amino acid selected from the group consisting of racemic, D-, and L-amino acids;
n is 1 or 2;
$R_1$ is selected from the group consisting of:
—R$_4$,
—X—R$_4$,
—X—Y—R$_4$, and
—X—R$_5$;
$R_3$ is selected from the group consisting of:
—Z—Ar,
—Z—Ar'—Y—R$_4$, and
—Z—Ar'—X—Y—R$_4$;
Ar is selected from the group consisting of aryl and heteroaryl both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, amino, alkylamino, and dialkylamino;
Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, amino, alkylamino, and dialkylamino;
X is alkylene optionally interrupted by one —O— group;
Y is selected from the group consisting of:
—O—,
—C(R$_6$)—,
—C(R$_6$)—N(R$_8$)—,
—S(O)$_{0-2}$—,
—N(R$_8$)-Q-, Z is selected from the group consisting of a bond and alkylene;
$R_4$ is selected from the group consisting of hydrogen, alkyl, alkenyl, aryl, arylalkylenyl, heteroaryl, heteroarylalkylenyl, and heterocyclyl, wherein the alkyl, alkenyl, aryl, arylalkylenyl, heteroaryl, heteroarylalkylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and, in the case of alkyl, alkenyl, and heterocyclyl, oxo;
$R_5$ is selected from the group consisting of:

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_{10}$ is $C_{3-8}$ alkylene;
A is selected from the group consisting of —O—, —C(O)—, —CH$_2$—, —S(O)$_{0-2}$—, and —N(Q-R$_4$)—;
Q is selected from the group consisting of a bond, —C(R$_6$)—, —S(O)$_2$, —C(R$_6$)—N(R$_8$)—, —S(O)$_2$—N(R$_8$)—, —C(R$_6$)—O—, and —C(R$_6$)—S—; and a and b are independently integers from 1 to 6 with the proviso that a+b is ≦7;

or a pharmaceutically acceptable salt thereof.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinoline-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring Systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene," "heteroarylene," and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N($R_8$)—C(O)—N($R_8$)— each $R_8$ group is independently selected. In another example, when $R_1$ and $R_3$ each contain an $R_4$ group then each $R_4$ group is independently selected. In a further example, when two Y groups are present and each Y group contains one or more $R_8$ groups, then each Y group and each $R_8$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound including any of the salt, solvated, polymorphic, or isomeric forms described above. The prodrug, itself, may be an immune response modifying compound including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., Y, X, Z, $R_1$, $R_3$, Q, $G_1$, $G_2$, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formula I, II, or III, n is 1.

For certain embodiments of Formula I, II, or III, n is 2.

For certain embodiments of Formula I, II, or III, including any one of the above embodiments, $R_1$ is selected from the group consisting of alkyl, aminoalkyl, dihydroxyalkyl, haloalkyl, and hydroxyalkyl. For certain of these embodiments, $R_1$ is selected from the group consisting of methyl, ethyl, n-propyl, n-butyl, 2-methylpropyl, 2-amino-2-methylpropyl, 3-amino-2,2-dimethylpropyl, 2,3-dihydroxypropyl, 2-fluoro-2-methylpropyl, and 2-hydroxy-2-methylpropyl. Alternatively, for certain of these embodiments, $R_1$ is selected from the group consisting of (1-hydroxycyclobutyl)methyl, (1-hydroxycyclopentyl)methyl, and (1-hydroxycyclohexyl) methyl.

For certain embodiments of Formula I, II, or III, including any one of the above embodiments, $R_1$ is heterocyclylalkylenyl wherein heterocyclyl is unsubstituted or substituted by one or more substituents independently selected from the group consisting of $C_{1-4}$ alkyl, hydroxy, and oxo, except where $R_1$ as defined does not include this definition. For certain of these embodiments, $R_1$ is other than 3-(2-oxopyrrolidin-1-yl)propyl when $R_3$ is phenyl or pyridin-4-yl. For certain of these embodiments, heterocyclyl is selected from the group consisting of 1,3-dioxolanyl, tetrahydropyranyl, tetrahydrofuranyl, pyrrolidinyl, piperidinyl, and morpholinyl, and alkylenyl is $C_{1-4}$ alkylenyl. For certain of these embodiments, heterocyclyl is selected from the group consisting of 1,3-dioxolanyl, tetrahydropyranyl, tetrahydrofuranyl, piperidinyl, and morpholinyl, and alkylenyl is $C_{1-4}$ alkylenyl. For certain of these embodiments, as well as any one of the above embodiments, $R_1$ is selected from the group consisting of tetrahydro-2H-pyran-4-ylmethyl and (2,2-dimethyl-1,3-dioxolan-4-yl)methyl, except where $R_1$ as defined does not include this definition. Alternatively, for certain of these embodiments, $R_1$ is (4-hydroxytetrahydro-2H-pyran-4-yl)methyl.

For certain embodiments of Formula I, II, or III, $R_1$ is other than 3-(2-oxopyrrolidin-1-yl)propyl when $R_3$ is phenyl or pyridin-4-yl.

For certain embodiments of Formula I, II, or III, including any one of the above embodiments, $R_1$ is —X—Y—$R_4$, except where $R_1$ as defined does not include this definition, wherein X is $C_{1-6}$ alkylene which may be interrupted by one —O— group; Y is selected from the group consisting of —N($R_8$)—C(O)—, —N($R_8$)—S(O)$_2$—, —N($R_8$)—C(O)—N($R_8$)—, and —S(O)$_2$— wherein $R_8$ is selected from hydrogen and methyl; and $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl. For certain of these embodiments, as well as any one of the above embodiments, $R_1$ is selected from the group consisting of 2-[(cyclopropylcarbonyl)amino] ethyl, 4-[(cyclopropylcarbonyl)amino]butyl, 2-[(cyclohexylcarbonyl)amino]-2-methylpropyl, 2-{[(1-methylethyl)carbonyl]amino}ethyl, 4-{[(1-methylethyl)carbonyl] amino}butyl, 2-methyl-2-{[(1-methylethyl)carbonyl] amino}propyl, 2-[(methylsulfonyl)amino]ethyl, 4-[(methylsulfonyl)amino]butyl, 2-methyl-2-[(methylsulfonyl)amino]propyl, 2-methyl-2-({[(1-methylethyl)amino] carbonyl}amino)propyl, 2-methyl-2-[2-(methylsulfonyl) ethoxy]propyl, and 2,2-dimethyl-3-(methylsulfonyl)propyl, except where $R_1$ as defined does not include this definition. Alternatively, for certain of these embodiments, $R_1$ is selected from the group consisting of 4-(propylaminocarbonylamino) butyl, 4-(propylcarbonylamino)butyl, 4-(cyclopentylaminocarbonylamino)butyl, and 4-(cyclopentylcarbonylamino) butyl.

For certain embodiments of Formula I, II, or III, including any one of the above embodiments, $R_1$ is —X—Y—$R_4$, except where $R_1$ as defined does not include this definition, wherein X is $C_{1-6}$ alkylene which may be interrupted by an —O— group; Y is selected from the group consisting of —N($R_8$)—C(O)—, —N($R_8$)—S(O)$_2$—, —N($R_8$)—C(O)—N($R_8$)—, —N($R_8$)—S(O)$_2$—N($R_8$)—, —S(O)$_2$—, and

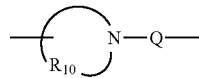

wherein Q is —C(O)—, —C(O)—NH—, or S(O)$_2$—, $R_{10}$ is pentylene, $R_8$ is hydrogen or methyl; and $R_4$ is selected from the group consisting of $C_{1-6}$ alkyl, hydroxyC$_{1-6}$ alkyl, isoquinolinyl, N-methylimidazolyl, pyridinyl, quinolinyl, benzyl, 1-phenylethyl, phenyl, and phenyl substituted by a substituent selected from the group consisting of chloro, cyano, fluoro, hydroxy, and methyl. For certain of these embodiments, X is $C_{1-6}$ alkylene, Y is selected from the group consisting of —N($R_8$)—C(O)—, —N($R_8$)—S(O)$_2$—, and —N($R_8$)—C(O)—N($R_8$)—, and $R_4$ is selected from the group consisting of $C_{1-4}$ alkyl, hydroxyC$_{1-4}$ alkyl, pyridinyl, benzyl, 1-phenylethyl, phenyl, and phenyl substituted by a substituent selected from the group consisting of chloro, cyano, fluoro, hydroxy, and methyl. Alternatively, for certain of these embodiments, X is $C_{1-6}$ alkylene, Y is

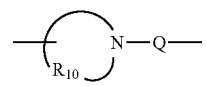

wherein Q is —C(O)—, —C(O)—NH—, or S(O)$_2$—, and $R_{10}$ is pentylene, and $R_4$ is $C_{1-4}$ alkyl. For certain of these embodiments where Y is

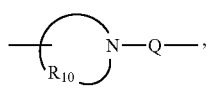

X is methylene. Alternatively, for certain of these embodiments, Y is —NH—S(O)$_2$—N($R_8$)—, $R_8$ is methyl, and $R_4$ is $C_{1-4}$ allyl. For certain of these embodiments where Y is —NH—S(O)$_2$—N($R_8$)—, X is $C_{2-6}$ alkylene.

For certain embodiments of Formula I, II, or III, including any one of the above embodiments, $R_1$ is —X—$R_5$, except where $R_1$ as defined does not include this definition, wherein X is $C_{1-6}$ alkylene, and $R_5$ is

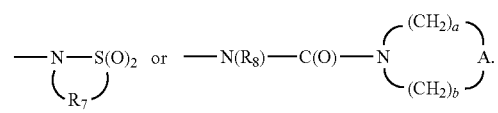

For certain of these embodiments, $R_5$ is

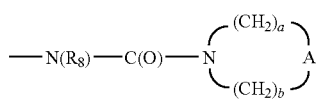

wherein $R_8$ is hydrogen, A is —O—, —CH$_2$—, or —N(Q-$R_4$)—, and a and b are each 2. For certain of these embodiments, Q-$R_4$ is methyl. Alternatively, for certain of these embodiments, $R_5$ is

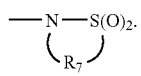

For certain of these embodiments, as well as any one of the above embodiments, $R_1$ is selected from the group consisting of 4-(1,1-dioxidoisothiazolidin-2-yl)butyl, 4-[(4-morpholinecarbonyl)amino]butyl, and 2-[(4-morpholinecarbonyl)amino]ethyl, except where $R_1$ as defined does not include this definition.

For certain embodiments of Formula I, II, or III, including any one of the above embodiments, $R_1$ is —X—$R_5$, except where $R_1$ as defined does not include this definition, wherein X is $C_{1-4}$ alkylene, and $R_5$ is

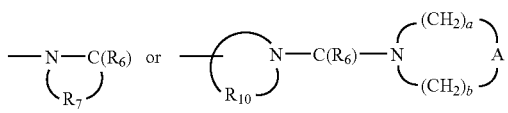

wherein $R_6$ is =O, $R_7$ is propylene, $R_{10}$ is pentylene, A is —O—, and a and b are each 2. For certain of these embodiments, $R_1$ is other than 3-(2-oxopyrrolidin-1-yl)propyl when $R_3$ is phenyl or pyridin-4-yl.

For certain embodiments of Formula I, II, or III, including any one of the above embodiments, Z is a bond.

For certain embodiments of Formula I, II, or III, including any one of the above embodiments, $R_3$ is phenyl, pyridin-2-yl, pyridin-3-yl, pyridin-4-yl, or quinolin-3-yl any of which may be unsubstituted or substituted by one or more substituents selected from the group consisting of alkyl, alkoxy, halogen, hydroxy, and hydroxyalkyl. For certain of these embodiments, when phenyl is substituted by alkyl, alkyl is at the 3-position of the phenyl group. For certain of these embodiments, $R_3$ is selected from the group consisting of pyridin-3-yl, pyridin-4-yl, 6-fluoropyridin-3-yl, 5-(hydroxymethyl)pyridin-3-yl, 2-ethoxyphenyl, and quinolin-3-yl.

For certain embodiments of Formula I, II, or III, including any one of the above embodiments, $R_3$ is thien-3-yl, phenyl, pyridin-2-yl, pyridin-3-yl, pyridin-4-yl, or quinolin-3-yl any of which may be unsubstituted or substituted by one or more substituents selected from the group consisting of alkyl, alkoxy, halogen, cyano, hydroxy, and hydroxyalkyl, except where $R_3$ as defined does not include this definition. For certain of these embodiments, when phenyl is substituted by alkyl, alkyl is at the 3-position of the phenyl group.

For certain embodiments of Formula I, II, or III, including any one of the above embodiments, $R_3$ is -Ar'-Y—$R_4$, except where $R_3$ as defined does not include this definition, wherein Ar' is phenylene, Y is selected from the group consisting of —C(O)—, —C(O)—N($R_8$)—, —N($R_8$)—C(O)—, —N($R_8$)—S(O)$_2$—, and —N($R_8$)—C(O)—N($R_8$)— wherein $R_8$ is selected from hydrogen and methyl; and $R_4$ is selected from the group consisting of $C_{1-6}$ alkyl, morpholin-4-yl, phenyl, and phenyl substituted by a substituent selected from the group consisting of alkyl, alkoxy, halogen, hydroxy, and hydroxyalkyl.

For certain embodiments of Formula I, II, or III, including any one of the above embodiments, except where $R_3$ as defined does not include this definition, $R_3$ is -Ar'-Y—$R_4$, wherein Ar' is phenylene, Y is selected from the group consisting of —C(O)—, —C(O)—N($R_8$)—, —N($R_8$)—C(O)—, —N($R_8$)—S(O)$_2$—, and —N($R_8$)—C(O)—N($R_8$)— wherein $R_8$ is selected from hydrogen and methyl; and $R_4$ is selected from the group consisting of $C_{1-6}$ alkyl, phenyl, and phenyl substituted by a substituent selected from the group consisting of alkyl, alkoxy, halogen, hydroxy, and hydroxyalkyl; with the proviso that when Y is —C(O)—N($R_8$)— or —N($R_8$)—C(O)—N($R_8$)— then $R_4$ can also be hydrogen; and with the further proviso that when Y is —C(O)— or —N($R_8$)—C(O)— then $R_4$ can also be morpholin-4-yl, piperidin-1-yl, or pyrrolidin-1-yl. For certain of these embodiments, Y is —C(O)—NH—, and $R_4$ is hydrogen or $C_{1-4}$ alkyl. For certain of these embodiments, $R_4$ is hydrogen. Alternatively, for certain of these embodiments, Y is —NH—C(O)—, and $R_4$ is $C_{1-4}$ alkyl. Alternatively, for certain of these embodiments, Y is —C(O)—, and $R_4$ is morpholin-4-yl, piperidin-1-yl, or pyrrolidin-1-yl. For certain of these embodiments, $R_3$ is 3-(methylsulfonylamino)phenyl, 3-(pyrrolidin-1-ylcarbonyl)phenyl, or 3-(morpholin-4-ylcarbonyl)phenyl.

For certain embodiments, for example, embodiments of Formula I, the present invention provides a compound selected from the group consisting of 2-hydroxymethyl-1-(2-methylpropyl)-7-phenyl-1H-imidazo[4,5-c]quinolin-4-amine, 2-(2-hydroxyethyl)-1-(2-methylpropyl)-7-phenyl-1H-imidazo[4,5-c]quinolin-4-amine, 1-(4-amino-2-hydroxymethyl-7-phenyl-1H-imidazo[4,5-c]quinolin-1-yl)-2-methylpropan-2-ol, and 1-[4-amino-2-(2-hydroxyethyl)-7-phenyl-1H-imidazo[4,5-c]quinolin-1-yl]-2-methylpropan-2-ol, or a pharmaceutically acceptable salt thereof.

For certain embodiments, for example, embodiments of Formula I, the present invention provides a compound selected from the group consisting of N-[4-(4-amino-2-hydroxymethyl-7-phenyl-1H-imidazo[4,5-c]quinolin-1-yl)butyl]methanesulfonamide and N-{4-[4-amino-2-(2-hydroxyethyl)-7-phenyl-1H-imidazo[4,5-c]quinolin-1-yl]butyl]}methanesulfonamide, or a pharmaceutically acceptable salt thereof.

For certain embodiments, for example, embodiments of Formula I, the present invention provides a compound selected from the group consisting of 2-hydroxymethyl-1-(2-methylpropyl)-7-(pyridin-3-yl)-1H-imidazo[4,5-c]quinolin-4-amine, 2-(2-hydroxyethyl)-1-(2-methylpropyl)-7-(pyridin-3-yl)-1H-imidazo[4,5-c]quinolin-4-amine, 1-[4-amino-2-hydroxymethyl-7-(pyridin-3-yl)-1H-imidazo[4,5-c]quinolin-1-yl]-2-methylpropan-2-ol, and 1-[4-amino-2-(2-hydroxyethyl)-7-(pyridin-3-yl)-1H-imidazo[4,5-c]quinolin-1-yl]-2-methylpropan-2-ol, or a pharmaceutically acceptable salt thereof.

For certain embodiments, for example, embodiments of Formula I, the present invention provides a compound selected from the group consisting of N-{4-[4-amino-2-hydroxymethyl-7-(pyridin-3-yl)-1H-imidazo[4,5-c]quinolin-1-yl]butyl]}methanesulfonamide and N-{4-[4-amino-2-(2-hydroxyethyl)-7-(pyridin-3-yl)-1H-imidazo[4,5-c]quinolin-1-yl]butyl]}methanesulfonamide, or a pharmaceutically acceptable salt thereof.

For certain embodiments, the present invention provides a pharmaceutical composition comprising a therapeutically effective amount of a compound or salt of Formula I, II, III, or of any one of the above embodiments and a pharmaceutically acceptable carrier.

For certain embodiments, the present invention provides a method of preferentially inducing the biosynthesis of IFN-α in an animal comprising administering an effective amount of a compound or salt of Formula I, II, III, or of any one of the above embodiments or the above pharmaceutical composition to the animal.

For certain embodiments, the present invention provides a method of treating a viral disease in an animal in need thereof comprising administering a therapeutically effective amount of a compound or salt of Formula I, II, III, or of any one of the above embodiments or the above pharmaceutical composition to the animal. For certain of these embodiments, the method includes preferentially inducing the biosynthesis of IFN-α. For certain embodiments, the present invention provides a method of treating a neoplastic disease in an animal in need thereof comprising administering a therapeutically effective amount of a compound or salt of Formula I, II, III, or of any one of the above embodiments or the above pharmaceutical composition to the animal. For certain of these embodiments, the method includes preferentially inducing the biosynthesis of IFN-α.

For certain embodiments of the above methods, the compound or salt or pharmaceutical composition is administered systemically.

For certain embodiments, $R_1$ is selected from the group consisting of —$R_4$, —X—$R_4$, —X—Y—$R_4$, and —X—$R_5$.

For certain embodiments, $R_1$ is —$R_4$.

For certain embodiments, $R_1$ is selected from the group consisting of alkyl, aminoalkyl, dihydroxyalkyl, haloalkyl, and hydroxyalkyl.

For certain embodiments, $R_1$ is selected from the group consisting of methyl, ethyl, n-propyl, n-butyl, 2-methylpropyl, 2-amino-2-methylpropyl, 3-amino-2,2-dimethylpropyl, 2,3-dihydroxypropyl, 2-fluoro-2-methylpropyl, and 2-hydroxy-2-methylpropyl.

For certain embodiments, $R_1$ is selected from the group consisting of (1-hydroxycyclobutyl)methyl, (1-hydroxycyclopentyl)methyl, and (1-hydroxycyclohexyl)methyl.

For certain embodiments, $R_1$ is heterocyclylalkylenyl wherein heterocyclyl is unsubstituted or substituted by one or more substituents independently selected from the group consisting of $C_{1-4}$ alkyl, hydroxy, and oxo. For certain of these embodiments, $R_1$ is other than 3-(2-oxopyrrolidin-1-yl)propyl when $R_3$ is phenyl or pyridin-4-yl.

For certain embodiments, $R_1$ is heterocyclylalkylenyl wherein heterocyclyl is selected from the group consisting of 1,3-dioxolanyl, tetrahydropyranyl, tetrahydrofuranyl, pyrrolidinyl, piperidinyl, and morpholinyl, and alkylenyl is $C_{1-4}$ alkylenyl.

For certain embodiments, $R_1$ is selected from the group consisting of tetrahydro-2H-pyran-4-ylmethyl and (2,2-dimethyl-1,3-dioxolan-4-yl)methyl.

For certain embodiments, $R_1$ is (4-hydroxytetrahydro-2H-pyran-4-yl)methyl.

For certain embodiments, $R_1$ is —X—Y—$R_4$.

For certain embodiments, $R_1$ is —X—Y—$R_4$ wherein X is $C_{1-6}$ alkylene which may be interrupted by one —O— group; Y is selected from the group consisting of —N($R_8$)—C(O)—, —N($R_8$)—S(O)$_2$—, —N($R_8$)—C(O)—N($R_8$)—, and —S(O)$_2$— wherein $R_8$ is selected from hydrogen and methyl; and $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl.

For certain embodiments, $R_1$ is selected from the group consisting of 2-[(cyclopropylcarbonyl)amino]ethyl, 4-[(cyclopropylcarbonyl)amino]butyl, 2-[(cyclohexylcarbonyl)amino]-2-methylpropyl, 2-{[(1-methylethyl)carbonyl]amino}ethyl, 4-{[(1-methylethyl)carbonyl]amino}butyl, 2-methyl-2-{[(1-methylethyl)carbonyl]amino}propyl, 2-[(methylsulfonyl)amino]ethyl, 4-[(methylsulfonyl)amino]butyl, 2-methyl-2-[(methylsulfonyl)amino]propyl, 2-methyl-2-({[(1-methylethyl)amino]carbonyl}amino)propyl, 2-methyl-2-[2-(methylsulfonyl)ethoxy]propyl, and 2,2-dimethyl-3-(methylsulfonyl)propyl.

For certain embodiments, $R_1$ is —X—Y—$R_4$ wherein X is $C_{1-6}$ alkylene which may be interrupted by an —O— group; Y is selected from the group consisting of —N($R_8$)—C(O)—, —N($R_8$)—S(O)$_2$—, —N($R_8$)—C(O)—N($R_8$)—, —N($R_8$)—S(O)$_2$—N($R_8$)—, —S(O)$_2$—, and

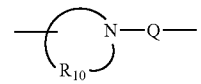

wherein Q is —C(O)—, —C(O)—NH—, or S(O)$_2$—, $R_{10}$ is pentylene, $R_8$ is hydrogen or methyl; and $R_4$ is selected from the group consisting of $C_{1-6}$ alkyl, hydroxy$C_{1-6}$ alkyl, isoquinolinyl, N-methylimidazolyl, pyridinyl, quinolinyl, benzyl, 1-phenylethyl, phenyl, and phenyl substituted by a substituent selected from the group consisting of chloro, cyano, fluoro, hydroxy, and methyl.

For certain embodiments, $R_1$ is —X—Y—$R_4$ wherein X is $C_{1-4}$ alkylene; Y is

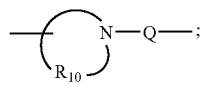

and $R_4$ is $C_{1-4}$ alkyl. For certain of these embodiments, $R_{10}$ is pentylene, and Q is selected from the group consisting of —S(O)$_2$—, —C(O)—, and —C(O)—NH—.

For certain embodiments, $R_1$ is —X—Y—$R_4$ wherein Y is —NH—S(O)$_2$—N($R_8$)—, $R_8$ is methyl, and $R_4$ is $C_{1-4}$ alkyl.

For certain embodiments, $R_1$ is —X—$R_5$.

For certain embodiments, $R_1$ is —X—$R_5$ wherein X is $C_{1-6}$ alkylene, and $R_5$ is

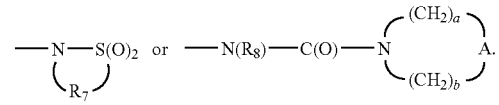

For certain embodiments, $R_1$ is —X—$R_5$ wherein X is $C_{1-6}$ alkylene, and $R_5$ is

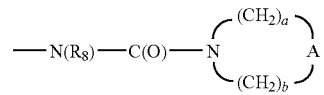

wherein $R_8$ is hydrogen, A is —O—, —CH$_2$—, or —N(Q-$R_4$)—, and a and b are each 2.

For certain embodiments, $R_1$ is —X—$R_5$ wherein X is $C_{1-6}$ alkylene, $R_5$ is

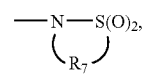

and $R_7$ is propylene.

For certain embodiments, $R_1$ is —X—$R_5$, wherein X is $C_{1-4}$ alkylene, and $R_5$ is

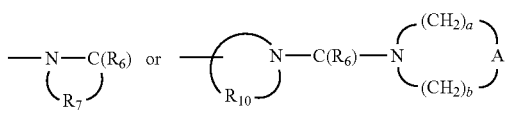

wherein $R_6$ is =O, $R_7$ is propylene, $R_{10}$ is pentylene, A is —O—, and a and b are each 2. For certain of these embodiments, $R_1$ is other than 3-(2-oxopyrrolidin-1-yl)propyl when $R_3$ is phenyl or pyridin-4-yl.

For certain embodiments, $R_1$ is selected from the group consisting of 4-(1,1-dioxidoisothiazolidin-2-yl)butyl, 4-[(4-morpholinecarbonyl)amino]butyl, and 2-[(4-morpholinecarbonyl)amino]ethyl.

For certain embodiments, $R_3$ is selected from the group consisting of —Z—Ar, —Z—Ar'-Y—$R_4$, and —Z—Ar'-X—Y—$R_4$.

For certain embodiments, $R_3$ is —Z—Ar.

For certain embodiments, $R_3$ is thien-3-yl, phenyl, pyridin-2-yl, pyridin-3-yl, pyridin-4-yl, or quinolin-3-yl any of which may be unsubstituted or substituted by one or more substituents selected from the group consisting of alkyl, alkoxy, halogen, cyano, hydroxy, and hydroxyalkyl. For certain of these embodiments, when phenyl is substituted by alkyl, alkyl is at the 3-position of the phenyl group.

For certain embodiments, $R_3$ is phenyl, pyridin-2-yl, pyridin-3-yl, pyridin-4-yl, or quinolin-3-yl any of which may be unsubstituted or substituted by one or more substituents selected from the group consisting of alkyl, alkoxy, halogen, hydroxy, and hydroxyalkyl. For certain of these embodiments, when phenyl is substituted by alkyl, alkyl is at the 3-position of the phenyl group.

For certain embodiments, $R_3$ is selected from the group consisting of pyridin-3-yl, pyridin-4-yl, 6-fluoropyridin-3-yl, 5-(hydroxymethyl)pyridin-3-yl, 2-ethoxyphenyl, and quinolin-3-yl.

For certain embodiments, $R_3$ is -Ar'-Y—$R_4$.

For certain embodiments, $R_3$ is -Ar'-Y—$R_4$ wherein Ar' is phenylene, Y is selected from the group consisting of —C(O)—, —C(O)—N($R_8$)—, —N($R_8$)—C(O)—, —N($R_8$)—S(O)$_2$—, and —N($R_8$)—C(O)—N($R_8$)— wherein $R_8$ is selected from hydrogen and methyl; and $R_4$ is selected from the group consisting of $C_{1-6}$ alkyl, phenyl, morpholin-4-yl, and phenyl substituted by a substituent selected from the group consisting of alkyl, alkoxy, halogen, hydroxy, and hydroxyalkyl.

For certain embodiments, $R_3$ is -Ar'-Y—$R_4$, wherein Ar' is phenylene, Y is selected from the group consisting of —C(O)—, —C(O)—N($R_8$)—, —N($R_8$)—C(O)—, —N($R_8$)—S(O)$_2$—, and —N($R_8$)—C(O)—N($R_8$)— wherein $R_8$ is selected from hydrogen and methyl; and $R_4$ is selected from the group consisting of $C_{1-6}$ alkyl, phenyl, and phenyl substituted by a substituent selected from the group consisting of alkyl, alkoxy, halogen, hydroxy, and hydroxyalkyl; with the proviso that when Y is —C(O)—N($R_8$)— or —N($R_8$)—C(O)—N($R_8$)— then $R_4$ can also be hydrogen; and with the further proviso that when Y is —C(O)— or —N($R_8$)—C(O)— then $R_4$ can also be morpholin-4-yl, piperidin-1-yl, or pyrrolidin-1-yl.

For certain embodiments, $R_3$ is -Ar'-Y—$R_4$, wherein Ar' is phenylene, Y is —C(O)—NH—, and $R_4$ is hydrogen or $C_{1-4}$ alkyl.

For certain embodiments, $R_3$ is -Ar'-Y—$R_4$, wherein Ar' is phenylene, Y is —NH—C(O)—, and $R_4$ is $C_{1-4}$ alkyl.

For certain embodiments, $R_3$ is -Ar'-Y—$R_4$, wherein Ar' is phenylene, Y is —C(O)—, and $R_4$ is morpholin-4-yl, piperidin-1-yl, or pyrrolidin-1-yl.

For certain embodiments, $R_3$ is 3-(methylsulfonylamino) phenyl, 3-(pyrrolidin-1-ylcarbonyl)phenyl, or 3-(morpholin-4-ylcarbonyl)phenyl.

For certain embodiments, $R_3$ is -Ar'-X—Y—$R_4$ wherein Ar' is phenylene, X is $C_{1-4}$ alkylene, Y is selected from the group consisting of —N($R_8$)—C(O)—, —N($R_8$)—S(O)$_2$—, and —N($R_8$)—C(O)—N($R_8$)— wherein $R_8$ is selected from hydrogen and methyl; and $R_4$ is selected from the group consisting of $C_{1-6}$ alkyl, phenyl, and phenyl substituted by a substituent selected from the group consisting of alkyl, alkoxy, halogen, hydroxy, and hydroxyalkyl.

For certain embodiments, $R_4$ is selected from the group consisting of hydrogen, alkyl, alkenyl, aryl, arylalkylenyl, heteroaryl, heteroarylalkylenyl, and heterocyclyl, wherein the alkyl, alkenyl, aryl, arylalkylenyl, heteroaryl, heteroarylalkylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and, in the case of alkyl, alkenyl, and heterocyclyl, oxo.

For certain embodiments, $R_4$ is selected from the group consisting of $C_{1-6}$ alkyl, hydroxy$C_{1-6}$ alkyl, isoquinolinyl, N-methylimidazolyl, pyridinyl, quinolinyl, benzyl, 1-phenylethyl, phenyl, and phenyl substituted by a substituent selected from the group consisting of chloro, cyano, fluoro, hydroxy, and methyl.

For certain embodiments, $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl.

For certain embodiments, $R_4$ is selected from the group consisting of $C_{1-6}$ alkyl, morpholin-4-yl, phenyl, and phenyl substituted by a substituent selected from the group consisting of alkyl, alkoxy, halogen, hydroxy, and hydroxyalkyl.

For certain embodiments, $R_4$ is selected from the group consisting of $C_{1-6}$ alkyl, phenyl, and phenyl substituted by a substituent selected from the group consisting of alkyl, alkoxy, halogen, hydroxy, and hydroxyalkyl.

For certain embodiments, $R_4$ is morpholin-4-yl, piperidin-1-yl, or pyrrolidin-1-yl.

For certain embodiments, $R_4$ is $C_{1-6}$ alkyl.

For certain embodiments, $R_4$ is hydrogen or $C_{1-4}$ alkyl.

For certain embodiments, $R_4$ is $C_{1-4}$ alkyl.

For certain embodiments, $R_4$ is hydrogen.

For certain embodiments, $R_5$ is selected from the group consisting of:

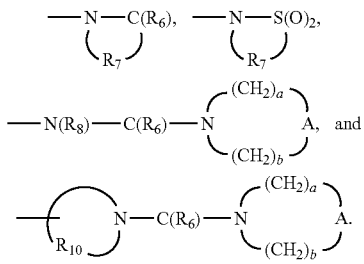

For certain of these embodiments, —X—$R_5$ is other than 3-(2-oxopyrrolidin-1-yl)propyl when $R_3$ is phenyl or pyridin-4-yl.

For certain embodiments, $R_5$ is

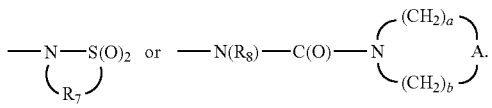

For certain embodiments, $R_5$ is

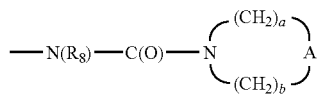

wherein $R_8$ is hydrogen, A is —O—, —$CH_2$—, or —N(Q-$R_4$)—, and a and b are each 2.

For certain embodiments, $R_5$ is

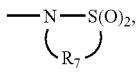

and $R_7$ is propylene.

For certain embodiments, $R_5$ is

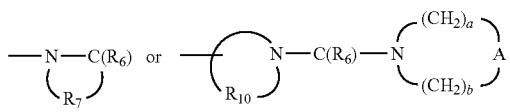

wherein $R_6$ is =O, $R_7$ is propylene, $R_{10}$ is pentylene, A is —O—, and a and b are each 2.

For certain embodiments, $R_6$ is selected from the group consisting of =O and =S.

For certain embodiments, $R_6$ is =O.

For certain embodiments, $R_6$ is =S.

For certain embodiments, $R_7$ is $C_{2-7}$ alkylene.

For certain embodiments, $R_7$ is $C_{2-4}$ alkylene.

For certain embodiments, $R_8$ is selected from the group consisting of hydrogen, alkyl, alkoxyalkylenyl, hydroxyalkylenyl, arylalkylenyl, and heteroarylalkylenyl.

For certain embodiments, $R_8$ is selected from the group consisting of hydrogen, $C_{1-4}$ alkyl, and $C_{1-4}$ alkoxy$C_{1-4}$ alkylenyl.

For certain embodiments, $R_8$ is hydrogen or $C_{1-4}$ alkyl.

For certain embodiments, $R_8$ is selected from hydrogen and methyl

For certain embodiments, $R_8$ is methyl.

For certain embodiments, $R_8$ is hydrogen.

For certain embodiments, $R_{10}$ is $C_{3-8}$ alkylene.

For certain embodiments, $R_{10}$ is $C_{4-6}$ alkylene.

For certain embodiments, $R_{10}$ is pentylene.

For certain embodiments, A is selected from the group consisting of —O—, —C(O)—, —$CH_2$—, —$S(O)_{0-2}$—, and —N(Q-$R_4$)—.

For certain embodiments, A is —O—, —$CH_2$—, —S—, or —$S(O)_2$—.

For certain embodiments, A is —O—, —$CH_2$—, or —N(Q-$R_4$)—.

For certain embodiments, A is —O— or —$S(O)_2$—.

For certain embodiments, A is —O—.

For certain embodiments, A is —$CH_2$—.

For certain embodiments, A is —N(Q-$R_4$)—.

For certain embodiments, A is —N($CH_3$)—.

For certain embodiments, Ar is selected from the group consisting of aryl and heteroaryl both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, amino, alkylamino, and dialkylamino.

For certain embodiments, Ar is aryl.

For certain embodiments, Ar is phenyl.

For certain embodiments, Ar is phenyl which may be unsubstituted or substituted by one or more substituents selected from the group consisting of alkyl, alkoxy, halogen, hydroxy, and hydroxyalkyl. For certain of these embodiments, alkyl is at the 3-position of the phenyl group.

For certain embodiments, Ar is heteroaryl.

For certain embodiments, Ar is pyridin-2-yl, pyridin-3-yl, pyridin-4-yl, or quinolin-3-yl any of which may be unsubstituted or substituted by one substituent selected from the group consisting of alkyl, alkoxy, halogen, hydroxy, and hydroxyalkyl.

For certain embodiments, Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, amino, alkylamino, and dialkylamino.

For certain embodiments, Ar' is phenylene.

For certain embodiments, Ar' is pyridnylene.

For certain embodiments, including any one of the above embodiments of Formula II, $G_1$ is selected from the group consisting of —C(O)—R', α-aminoacyl, α-aminoacyl-α-aminoacyl, —C(O)—O—R', —C(O)—N(R")R', —C(=NY')—R', —CH(OH)—C(O)—OY', —CH(O$C_{1-4}$ alkyl)$Y_0$, —$CH_2Y_1$, and —CH($CH_3$)$Y_1$; R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —$S(O)_2$—$NH_2$, with the proviso that R" can also be hydrogen; α-aminoacyl is an α-aminoacyl group derived from an α-amino acid selected from the group consisting of racemic, D-, and L-amino acids; Y' is selected from the group consisting of hydrogen, $C_{1-6}$ alkyl, and benzyl; $Y_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl; and $Y_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl.

For certain embodiments, including any one of the above embodiments of Formula II, $G_1$ is selected from the group consisting of —C(O)—R', α-aminoacyl, and —C(O)—O—R'. For certain of these embodiments, R' contains one to ten carbon atoms. For certain of these embodiments, α-aminoacyl is an α-$C_{2-11}$ aminoacyl group derived from an α-amino acid selected from the group consisting of racemic, D-, and L-amino acids containing a total of at least 2 carbon atoms and a total of up to 11 carbon atoms, and may also include one or more heteroatoms selected from the group consisting of O, S, and N.

For certain embodiments, including any one of the above embodiments of Formula III, $G_2$ is selected from the group consisting of —$X_2$—C(O)—R', α-aminoacyl, α-aminoacyl-α-aminoacyl, —$X_2$—C(O)—O—R', and —C(O)—N(R")R'. For certain of these embodiments, $X_2$ is selected from the group consisting of a bond; —$CH_2$—O—; —CH($CH_3$)—O—; —C($CH_3$)$_2$—O—; and, in the case of —$X_2$—C(O)—O—R', —$CH_2$—NH—; R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$, with the proviso that R" can also be hydrogen; and α-aminoacyl is an α-aminoacyl group derived from an α-amino acid selected from the group consisting of racemic, D-, and L-amino acids.

For certain embodiments, including any one of the above embodiments of Formula III, $G_2$ is selected from the group consisting of —C(O)—R' and α-aminoacyl, wherein R' is $C_{1-6}$ alkyl or phenyl which is unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—$CH_3$, —C(O)—O—$CH_3$, —C(O)—$NH_2$, —O—$CH_2$—C(O)—$NH_2$, —$NH_2$, and —S(O)$_2$—$NH_2$.

For certain embodiments, including any one of the above embodiments of Formula III $G_2$ is selected from the group consisting of α-amino-$C_{2-5}$ alkanoyl, $C_{2-6}$ alkanoyl, $C_{1-6}$ alkoxycarbonyl, and $C_{1-6}$ alkylcarbamoyl.

For certain embodiments, including any one of the above embodiments which include an α-aminoacyl group, α-aminoacyl is an α-aminoacyl group derived from a naturally occurring α-amino acid selected from the group consisting of racemic, D-, and L-amino acids.

For certain embodiments, including any one of the above embodiments which include an α-aminoacyl group, α-aminoacyl is an α-aminoacyl group derived from an α-amino acid found in proteins, wherein the amino acid is selected from the group consisting of racemic, D-, and L-amino acids.

For certain embodiments, the hydrogen atom of the hydroxy group of Formula II (including any one of its embodiments) is replaced by $G_2$, wherein $G_2$ is defined as in any one of the above embodiments of $G_2$.

For certain embodiments, Q is selected from the group consisting of a bond, —C($R_6$)—, —S(O)$_2$, —C($R_6$)—N($R_8$)—, —S(O)$_2$—N($R_8$)—, —C($R_6$)—O—, and —C($R_6$)—S—.

For certain embodiments, Q is selected from the group consisting of a bond, —C($R_6$)—, —S(O)$_2$—, and —C($R_6$)—N($R_8$)—.

For certain embodiments, Q is selected from the group consisting of —C(O)—, —S(O)$_2$—, and —C(O)—N($R_8$)—. In certain of these embodiments, $R_8$ is hydrogen or methyl.

For certain embodiments, Q is selected from the group consisting of —S(O)$_2$—, —C(O)—, and —C(O)—NH—.

For certain embodiments, Q is —C(O)—.
For certain embodiments, Q is —S(O)$_2$—.
For certain embodiments, Q is —C($R_6$)—N($R_8$)—.
For certain embodiments, Q is —C(O)—N($R_8$)— wherein $R_8$ is hydrogen or methyl.

For certain embodiments, X is alkylene which can be optionally interrupted or terminated by arylene and optionally interrupted by one —O— group.

For certain embodiments, X is $C_{1-6}$ alkylene which may be interrupted by one —O— group.

For certain embodiments, X is $C_{1-6}$ alkylene.
For certain embodiments, X is $C_{2-6}$ alkylene.
For certain embodiments, X is $C_{1-4}$ alkylene.
For certain embodiments, X is methylene.
For certain embodiments, X is ethylene.
For certain embodiments, X is butylene.

For certain embodiments, Y is selected from the group consisting of —O—, —C($R_6$)—, —C($R_6$)—N($R_8$)—, —S(O)$_{0-2}$—, —N($R_8$)-Q-,

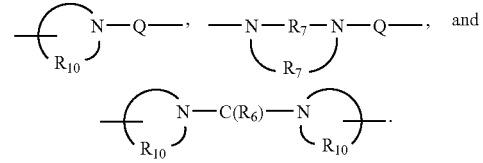

For certain embodiments, Y is selected from the group consisting of —N($R_8$)—C(O)—, —N($R_8$)—S(O)$_2$—, —N($R_8$)—C(O)—N($R_8$)—, —N($R_8$)—S(O)$_2$—N($R_8$)—, —S(O)$_2$—, and

In certain of these embodiments, Q is —C(O)—, —C(O)—NH—, or S(O)$_2$—, $R_{10}$ is pentylene, and $R_8$ is hydrogen or methyl.

For certain embodiments, Y is selected from the group consisting of —N($R_8$)—C(O)—, —N($R_8$)—S(O)$_2$—, —N($R_8$)—C(O)—N($R_8$)—, and —S(O)$_2$—. In certain of these embodiments, $R_8$ is selected from hydrogen and methyl.

For certain embodiments, Y is selected from the group consisting of —C(O)—, —C(O)—N($R_8$)—, —N($R_8$)—C(O)—, —N($R_8$)—S(O)$_2$—, and —N($R_8$)—C(O)—N($R_8$)— wherein $R_8$ is selected from hydrogen and methyl.

For certain embodiments, Y is selected from the group consisting of —N($R_8$)—C(O)—, —N($R_8$)—S(O)$_2$—, and —N($R_8$)—C(O)—N($R_8$)— wherein $R_8$ is selected from hydrogen and methyl.

For certain embodiments, Y is selected from the group consisting of —C(O)—, —N($R_8$)—C(O)—, —N($R_8$)—S(O)$_2$—, and —N($R_8$)—C(O)—N($R_8$)—. In certain of these embodiments, $R_8$ is selected from hydrogen and methyl.

For certain embodiments, Y is

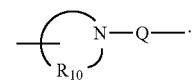

For certain of these embodiments, $R_{10}$ is pentylene, and Q is selected from the group consisting of —S(O)$_2$—, —C(O)—, and —C(O)—NH—.

For certain embodiments, Y is —NH—S(O)$_2$—N(R$_8$)—. In certain of these embodiments, $R_8$ is methyl.

For certain embodiments, Z is a bond.

For certain embodiments, Z is alkylene.

For certain embodiments, a and b are independently integers from 1 to 6 with the proviso that a+b is ≦7.

For certain embodiments, a and b are each independently 1 to 3.

For certain embodiments, a and b are each 2.

For certain embodiments, a is 1, 2, or 3, and b is 2.

For certain embodiments, n is 1 or 2.

For certain embodiments, n is 1.

For certain embodiments, n is 2.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

In some embodiments, compounds of the invention can be prepared according to Reaction Scheme I, wherein $R_1$, $R_3$, and n are as defined above and alkyl is methyl or ethyl.

In Reaction Scheme I an ether substituted 1H-imidazo[4,5-c]quinolin-4-amine of Formula X is cleaved to provide a hydroxyalkyl substituted 1H-imidazo[4,5-c]quinolin-4-amine of Formula I. The reaction is conveniently carried out by adding a solution of boron tribromide in a suitable solvent such as dichloromethane to a solution or suspension of a compound of Formula X in a suitable solvent such as dichloromethane at ambient or at a sub-ambient temperature, for example, at 0° C. The product or pharmaceutically acceptable salt thereof can be isolated using conventional methods.

Numerous compounds of Formula X are known; others can be prepared using known synthetic methods. See United States Patent Application Publication No. 2004/0147543 and the references cited therein.

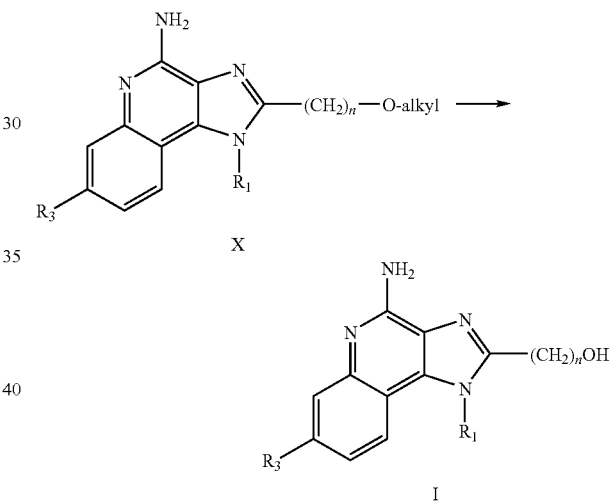

In some embodiments, compounds of the invention can also be prepared according to Reaction Scheme II, wherein $R_1$, $R_3$, and n are as defined above and alkyl is methyl or ethyl.

In step (1) of Reaction Scheme II, a 7-bromo 1H-imidazo[4,5-c]quinolin-4-amine of Formula XI is converted to a 1H-imidazo[4,5-c]quinolin-4-amine of Formula X. The reaction can be carried out using known palladium catalyzed coupling reactions such as Suzki coupling, Stille coupling, Sonogashira coupling, and the Heck reaction using the methods described in United States Patent Application Publication No. 2004/0147543.

Numerous compounds of Formula XI are known; others can be prepared using known synthetic methods. See United States Patent Application Publication No. 2004/0147543 and the references cited therein.

In step (2) of Reaction Scheme II, an ether substituted 1H-imidazo[4,5-c]quinolin-4-amine of Formula X is cleaved to provide a hydroxyalkyl substituted 1H-imidazo[4,5-c] quinolin-4-amine of Formula I using the method described in Reaction Scheme I.

Reaction Scheme II

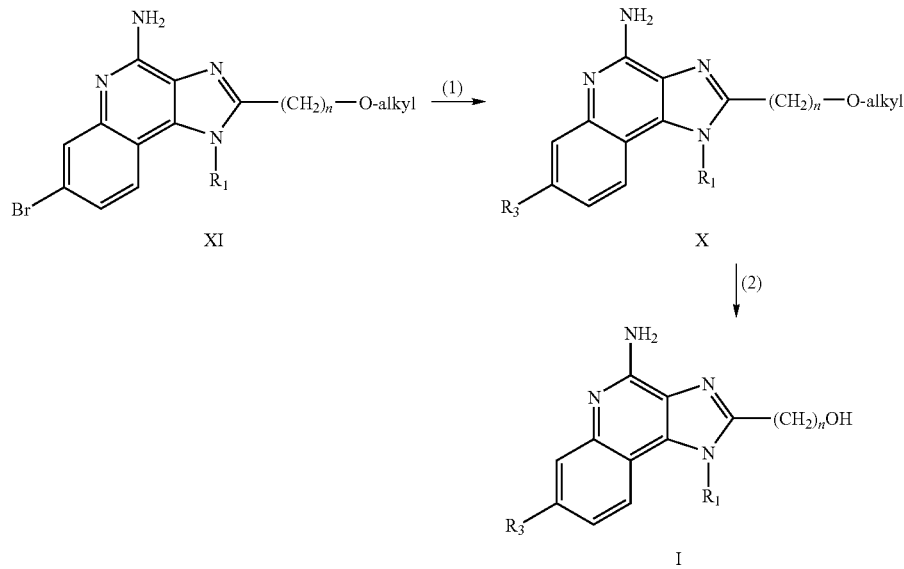

In some embodiments, compounds of the invention can also be prepared according to Reaction Scheme III, wherein $R_3$, $R_4$, Q, X, and n are as defined above and alkyl is methyl or ethyl.

In step (1) of Reaction Scheme III, the amino group on the —X—NH$_2$ substituent of a 1H-imidazo[4,5-c]quinolin-4-amine of Formula XII is further elaborated using conventional methods to provide 1H-imidazo[4,5-c]quinolin-4-amine of Formula XIII. For example, a compound of Formula XII can react with an acid chloride of Formula $R_4C(O)Cl$ to provide a compound of Formula XIII in which -Q-$R_4$ is —C(O)—$R_4$. In addition, a compound of Formula XII can react with sulfonyl chloride of Formula $R_4S(O)_2Cl$ or a sulfonic anhydride of Formula $(R_4S(O)_2)_2O$ to provide a compound of Formula XIII in which -Q-$R_4$ is —S(O)$_2$—$R_4$. Numerous acid chlorides of Formula $R_4C(O)Cl$, sulfonyl chlorides of Formula $R_4S(O)_2Cl$, and sulfonic anhydrides of Formula $(R_4S(O)_2)_2O$ are commercially available; others can be readily prepared using known synthetic methods. The reaction is conveniently carried out by adding the acid chloride of Formula $R_4C(O)Cl$, sulfonyl chloride of Formula $R_4S(O)_2Cl$, or sulfonic anhydride of Formula $(R_4S(O)_2)_2O$ to a solution of the compound of Formula XII in a suitable solvent such as chloroform, dichloromethane, or 1-methyl-2-pyrrolidinone. Optionally a base such as triethylamine, pyridine, or N,N-diisopropylethylamine, or a combination thereof can be added. The reaction can be carried out at room temperature or initially at a sub-ambient temperature such as 0° C. and then warming to room temperature. Ureas of Formula XIII, where -Q-$R_4$ is —C($R_6$)—NH—$R_4$ and $R_6$ is =O can be prepared by reacting a compound of Formula XII with isocyanates of Formula $R_4N$=C=O, Numerous isocyanates of Formula $R_4N$=C=O are commercially available; others can be readily prepared using known synthetic methods. The reaction can be conveniently carried out by adding the isocyanate of Formula $R_4N$=C=O to a solution of a compound of Formula XII in a suitable solvent such as dichloromethane or chloroform. Optionally a base such as triethylamine can be added. The reaction can be carried out at room temperature or initially at a sub-ambient temperature such as 0° C. and then warming to room temperature.

In step (2) of Reaction Scheme III, an ether substituted 1H-imidazo[4,5-c]quinolin-4-amine of Formula XIII is cleaved to provide a hydroxyalkyl substituted 1H-imidazo[4,5-c]quinolin-4-amine of Formula XIV, which is a subgenus of Formula I, using the method described in Reaction Scheme I.

Reaction Scheme III

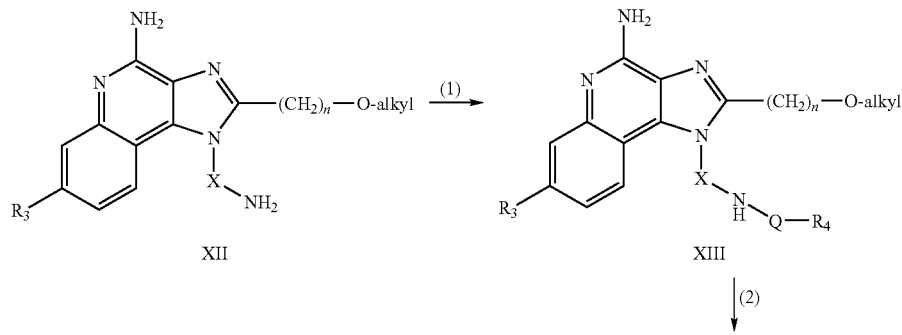

-continued

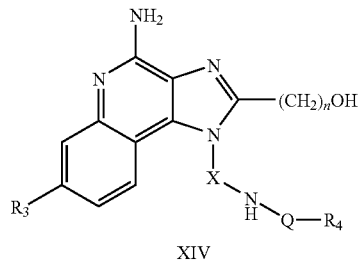

XIV

In some embodiments, compounds of the invention can be prepared according to Reaction Scheme IV, wherein $R_1$, $R_3$, $G_1$, and n are as defined above. Compounds of Formula I can be prepared according to the methods described above. The amino group of a compound of Formula I can be converted by conventional methods to a functional group such as an amide, carbamate, urea, amidine, or another hydrolyzable group. A compound of this type can be made by the replacement of a hydrogen atom in an amino group with a group such as —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$; wherein R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; each α-aminoacyl is an α-aminoacyl group derived from an α-amino acid selected from the group consisting of racemic, D-, and L-amino acids; Y' is selected from the group consisting of hydrogen, $C_{1-6}$ alkyl, and benzyl; Y$_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl; and Y$_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl. Particularly useful compounds of Formula II are amides derived from carboxylic acids containing one to ten carbon atoms, amides derived from amino acids, and carbamates containing one to ten carbon atoms. The reaction can be carried out, for example, by combining a compound of Formula I with a chloroformate or acid chloride, such as ethyl chloroformate or acetyl chloride, in the presence of a base such as triethylamine in a suitable solvent such as dichloromethane at ambient temperature.

Alternatively, the hydroxy group on a compound of Formula I can be protected using a suitable silyl group such as tert-butyl dimethylsilyl using conventional methods. The G$_1$ group may then be installed using conventional methods followed by the removal of the hydroxy protecting group under acidic conditions to provide a compound of Formula II.

Reaction Scheme IV

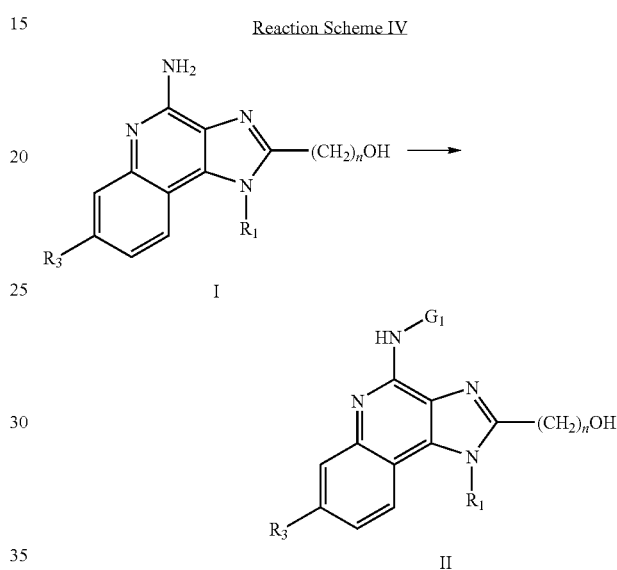

In some embodiments, compounds of the invention can be prepared according to Reaction Scheme V, wherein $R_1$, $R_3$, $G_2$, and n are as defined above. Compounds of Formula I can be prepared according to the methods described above. The hydrogen atom of the alcohol group of a compound of Formula I can be replaced using conventional methods with a group such as X$_2$—C(O)—R', α-aminoacyl, -aminoacyl-α-aminoacyl, —X$_2$—C(O)—O—R', and —C(O)—N(R")R'; wherein X$_2$ is selected from the group consisting of a bond; —CH$_2$—O—; —CH(CH$_3$)—O—; —C(CH$_3$)$_2$—O—; and, in the case of —X$_2$—C(O)—O—R', —CH$_2$—NH—; R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; and each α-aminoacyl is an α-aminoacyl group derived from an α-amino acid selected from the group consisting of racemic, D-, and L-amino acids. Particularly useful compounds of Formula III are esters made from carboxylic acids containing one to six carbon atoms, unsubstituted or substituted benzoic acid esters, or esters made from naturally occurring amino acids. For example, the reaction can be carried out by treating a compound of Formula I with a carboxylic acid or amino acid under Mitsunobu reaction conditions by adding triphenylphosphine and a carboxylic acid to a solution or suspension of a compound of Formula I in a suitable solvent such as tetrahydrofuran and then slowly adding diisopropyl azodicarboxylate. The reaction can be run at a sub-ambient temperature such as 0° C.

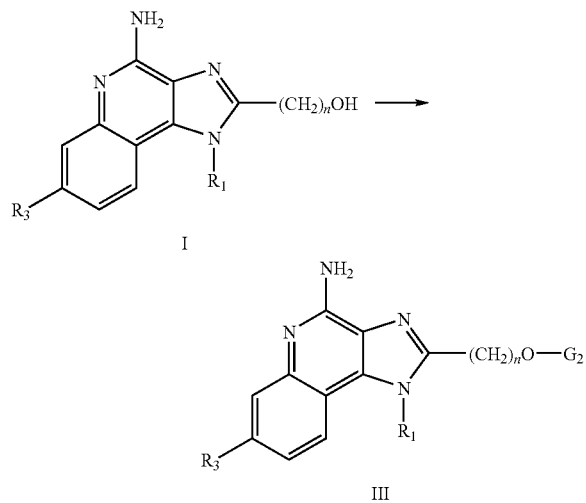

Reaction Scheme V

In some embodiments, compounds of the invention can also be prepared using the synthetic methods described in the EXAMPLES below.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Cytokine induction can include preferentially inducing the biosynthesis of IFN-α. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)× 0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as tablets, lozenges, capsules, parenteral formulations (e.g., intravenous formulations), syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders. The compounds or salts of the invention are especially useful as immune response modifiers due to their ability to preferentially induce interferon-α, thus providing a benefit over compounds that also induce pro-inflammatory cytokines (e.g. TNF-α) or that induce pro-inflammatory cytokines at higher levels. While interferon-α and pro-inflammatory cytokines are beneficial in treating certain conditions, interferon-α preferentially induced is believed to be better tolerated by patients, because the significantly lower levels of pro-inflammatory cytokines can result in fewer or less severe adverse side effects experienced by patients. For example, if a subject is treated for a disease (e.g., hepatitis C, metastatic cancer) with a compound that induces significant levels of pro-inflammatory cytokines, while treating the disease, the compound may also cause side effects, such as severe and/or widespread inflammation, tissue destruction, or emesis, that render the subject unable or unwilling to receive the treatment. Alternatively, if a subject is treated with a compound that preferentially induces interferon-α then the compound may treat the disease with less risk of adverse side effects from pro-inflammatory cytokines such as TNF-α. Therefore, by maintaining the ability to treat a condition and reducing adverse side effects, compounds that preferentially induce IFN-α provide an advantage over compounds that would also induce pro-inflammatory cytokines, such as TNF-α, at higher levels.

The ability of the compounds or salts of the invention to preferentially induce the biosynthesis of IFN-α may be particularly advantageous when administered systemically, since adverse side effects, including for example widespread inflammation, may be reduced or even eliminated. Compounds of the invention may be administered systemically in a number of ways, including but not limited to oral and intravenous administration.

Cytokines whose biosynthesis may be induced by compounds or salts of the invention include IFN-α, IP-10, MCP-1, and a variety of other cytokines. In some instances, cytokines such as TNF-α, IL-12 may be induced, albeit at significantly reduced levels. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, the compounds or salts may cause maturation of dendritic cells or proliferation and differentiation of B-lymphocytes.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such as chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythemia, multiple sclerosis, discoid lupus, alopecia greata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as dendritic cells and B-cells to produce an amount of one or more cytokines such as, for example, IFN-α, IP-10, and MCP-1 that is increased (induced) over a background level of such cytokines. The precise amount will vary according to factors known in the art but is expected to be a dose of about 100 ng/kg to about 50 mg/kg, preferably about 10 µg/kg to about 5 mg/kg. In other embodiments, the amount is expected to be a dose of, for example, from about 0.01 mg/m² to about 5.0 mg/m², (computed according to the Dubois method as described above) although in some embodiments the induction of cytokine biosynthesis may be performed by administering a compound or salt in a dose outside this range. In some of these embodiments, the method includes administering sufficient compound or salt or composition to provide a dose of from about 0.1 mg/m² to about 2.0 mg/m² to the subject, for example, a dose of from about 0.4 mg/m² to about 1.2 mg/m².

The invention provides a method of treating a disease which is responsive to the induction of cytokine biosynthesis, particularly the preferential induction of IFN-α, including a method of treating a viral infection in an animal and a method of treating a neoplastic disease in an animal, comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

Examples 1-6

A solution of boron tribromide in heptane (400 μL of 1 M) was added to a tube containing a chilled (0° C.) solution of a compound of Formula Xa (about 25 mg) in dichloromethane (1 mL). The tube was vortexed, maintained at 0° C. for 0.5 hour, and then shaken overnight at ambient temperature. The reaction mixture was diluted with methanol (1 mL) and hydrochloric acid (250 μL of 6 N), vortexed, and then the solvents were removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. Table 1 shows the structure of the starting material, a reference for the starting material, the structure of the resulting compound, and the observed accurate mass for the isolated trifluoroacetate salt.

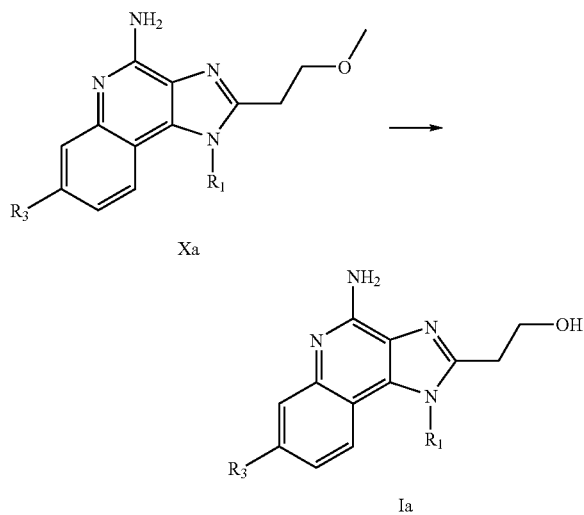

| Example | Reference Formula Xa | $R_1$ | $R_3$ | Measured Mass (M + H) |
|---|---|---|---|---|
| 1 | U.S. Patent Publication 2004/0147543 Example 206 | | | 430.2227 |

-continued

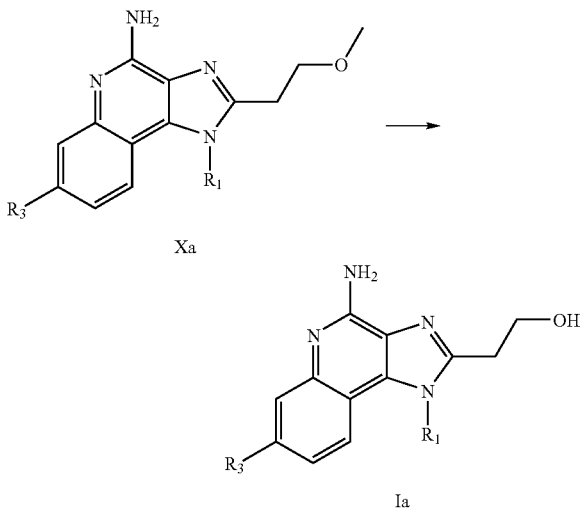
Xa

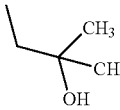
Ia

| Example | Reference Formula Xa | $R_1$ | $R_3$ | Measured Mass (M + H) |
|---|---|---|---|---|
| 2 | U.S. Patent Publication 2004/0147543 Example 136 | 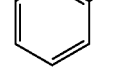 | 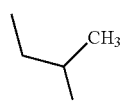 | 377.1985 |
| 3 | U.S. Patent Publication 2004/0147543 Example 145 | 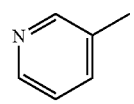 | 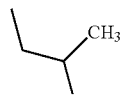 | 362.2008 |
| 4 | U.S. Patent Publication 2004/0147543 Example 146 | 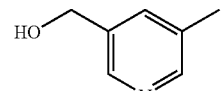 | 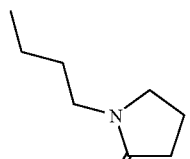 | 392.2104 |
| 5 | U.S. Patent Publication 2004/0147543 Example 183 | 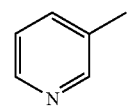 | 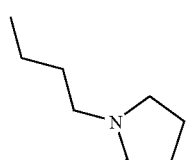 | 431.2209 |
| 6 | U.S. Patent Publication 2004/0147543 Example 184 | 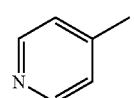 | | 431.2220 |

Examples 7-31

Part A 1-(4-Amino-7-bromo-2-ethoxymethyl-1H-imidazo[4,5-c]quinolin-1-yl)-2-methylpropan-2-ol (2 g, U.S. Patent Publication 2004/0147543 Example 125) was dissolved in 7:3 volume:volume chloroform:methanol (100 mL). Aliquots (2 mL, 1.0 eq.) were added to test tubes and the solvent was removed by vacuum centrifugation. A tube was charged with a boronic acid (1.1 eq) from the table below. n-Propanol (1.6 mL) was added to each tube, the tube was purged with nitrogen, and then sonicated until the contents were well mixed. Each tube was then charged sequentially with 150 μL of a solution of palladium (II) acetate in toluene (60 mg of palladium (II) acetate dissolved in 15 mL of toluene), 600 μL of 2 M aqueous sodium carbonate solution, 113 μL of water, and 53 μL of a 15 mole % solution of triphenylphosphine in n-propanol. The tubes were purged with nitrogen and then heated at 80° C. overnight.

The reaction mixtures were purified by solid phase extraction. Sufficient hydrochloric acid (1 N) was added to each reaction mixture to adjust the pH to ≦5. Each reaction mixture was loaded onto a cartridge (Waters Oasis Samples Extraction Cartridges MCX 6 cc). Methanol (5 mL) was added to each cartridge. The cartridge was placed in a clean test tube. The cartridge was eluted with two successive 5 mL portions of 1 N ammonia in methanol. The solvent was removed by vacuum centrifugation.

Part B

Dichloromethane (1 mL) was added to each tube, the tube was sonicated to dissolve the solids, and then the tube was chilled to 0° C. in an ice bath. A solution of boron tribromide in heptane (600 μL of 1 M) was added to each tube. The tube was vortexed, maintained at 0° C. for 0.5 hour, and then shaken overnight at ambient temperature. The solvents were removed by vacuum centrifugation. Methanol (1 mL) and hydrochloric acid (1 mL of 6 N) were added to each tube, the tubes were vortexed, and then the solvents were removed by vacuum centrifugation. The compounds were purified as described above for Examples 1-6. Table 2 shows the boronic acid, the structure of the resulting compound, and the observed accurate mass for the isolated trifluoroacetate salt.

TABLE 2

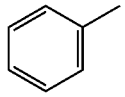

| Example | Reagent | $R_3$ | Measured Mass (M + H) |
|---|---|---|---|
| 7 | Phenylboronic acid | 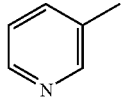 | 363.1847 |
| 8 | Pyridine-3-boronic acid | 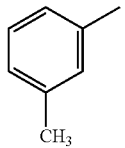 | 364.1779 |
| 9 | 3-Methylphenylboronic acid | 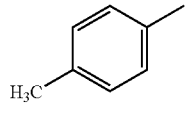 | 377.2001 |
| 10 | 4-Methylphenylboronic acid | 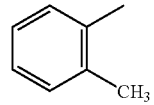 | 377.1979 |
| 11 | o-Tolylboronic acid | 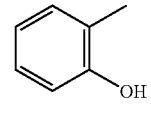 | 377.1990 |
| 12 | (2-Hydroxyphenyl)boronic acid | 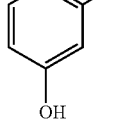 | 379.1776 |
| 13 | 3-Hydroxyphenylboronic acid |  | 379.1755 |

TABLE 2-continued

| Example | Reagent | R₃ | Measured Mass (M + H) |
|---|---|---|---|
| 14 | 3,5-Dimethylphenylboronic acid | 3,5-dimethylphenyl | 391.2130 |
| 15 | 4-(Hydroxymethyl)phenylboronic acid | 4-(hydroxymethyl)phenyl | 393.1935 |
| 16 | 3-Chlorophenylboronic acid | 3-chlorophenyl | 397.1432 |
| 17 | 2-Chlorophenylboronic acid | 2-chlorophenyl | 397.1447 |
| 18 | 4-Chlorophenylboronic acid | 4-chlorophenyl | 397.1431 |
| 19 | 2,4-Difluorophenylboronic acid | 2,4-difluorophenyl | 399.1642 |
| 20 | Benzo[b]furan-2-boronic acid | benzo[b]furan-2-yl | 403.1812 |
| 21 | (3-Aminocarbonylphenyl)boronic acid | 3-aminocarbonylphenyl | 406.1889 |
| 22 | 4-(N,N-Dimethylamino)phenylboronic acid | 4-(N,N-dimethylamino)phenyl | 406.2255 |

TABLE 2-continued

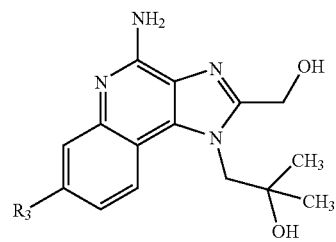

| Example | Reagent | R₃ | Measured Mass (M + H) |
|---|---|---|---|
| 23 | (3-Aminomethylphenyl)boronic acid hydrochloride | 3-(aminomethyl)phenyl | 392.2108 |
| 24 | 3,4-Dichlorophenylboronic acid | 3,4-dichlorophenyl | 431.1061 |
| 25 | 4-(Ethylsulfonyl)phenylboronic acid | 4-(ethylsulfonyl)phenyl | 455.1771 |
| 26 | 3-(Methylsulfonylamino)phenylboronic acid | 3-(methylsulfonylamino)phenyl | 456.1727 |
| 27 | 3-(Pyrrolidine-1-carbonyl)phenylboronic acid | 3-(pyrrolidine-1-carbonyl)phenyl | 460.2364 |
| 28 | 4-(Pyrrolidine-1-carbonyl)phenylboronic acid | 4-(pyrrolidine-1-carbonyl)phenyl | 460.2395 |

TABLE 2-continued

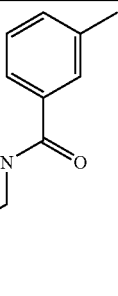

| Example | Reagent | R₃ | Measured Mass (M + H) |
|---|---|---|---|
| 29 | 3-(Butylaminocarbonyl)phenylboronic acid | 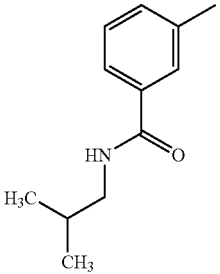 | 462.2488 |
| 30 | 3-(Isobutylaminocarbonyl)phenylboronic acid | 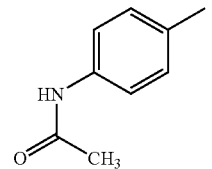 | 462.2527 |
| 31 | 4'-(4,4,5,5-Tetramethyl-1,3,2-dioxaborolan-2-yl)acetanilinde | 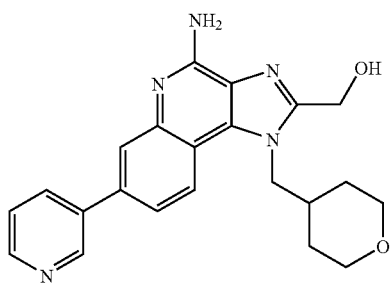 | 420.2022 |

Example 32

[4-Amino-7-pyridin-3-yl-1-(tetrahydro-2H-pyran-4-ylmethyl)-1H-imidazo[4,5-c]quinolin-2-yl]methanol

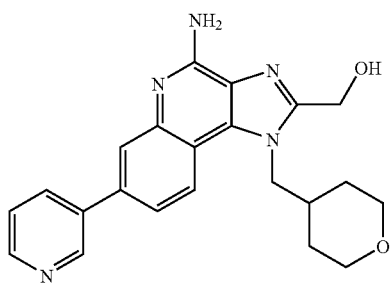

Part A

To a mixture of 1-tetrahydro-2H-pyran-4-ylmethanamine HCl (19 g, 120 mmol), dichloromethane (626 mL), and triethyl amine (43.7 mL, 313 mmol) was added 4-chloro-3-nitroquinolin at 0° C. The resulting bright yellow solution was stirred at ambient temperature for 18 hours. The reaction was then concentrated under reduced pressure. The resulting solid was stirred in water (100 mL) and filtered to give 43 g of 7-bromo-3-nitro-N-(tetrahydro-2H-pyran-4-ylmethyl)quinolin-4-amine as a yellow powder.

Part B

7-Bromo-3-nitro-N-(tetrahydro-2H-pyran-4-ylmethyl)quinolin-4-amine (20 g, 55 mmol) was dissolved in a mixture of acetonitrile (500 mL) and isopropyl alcohol (50 mL) and the solution was placed in a pressure bottle. Platinum on carbon (5%, 2 g) was then added and the reaction mixture was shaken under H₂ at 48 PSI ($3.3 \times 10^5$ Pa). After 2 hours, the reaction mixture was filtered through a pad of CELITE filter agent. The pad was rinsed with acetonitrile and the combined filtrates were concentrated under reduced pressure to give 7-bromo-N$^4$-(tetrahydro-2H-pyran-4-ylmethyl)quinoline-3,4-diamine which was carried forward without further purification assuming quantitative yield.

Part C

Chloroacetyl chloride (5.2 mL, 65 mmol) was added to 7-bromo-N$^4$-(tetrahydro-2H-pyran-4-ylmethyl)quinoline-3,4-diamine (55 mmol) dissolved in 273 mL of dichloromethane at 0° C. A solid formed after adding half of the chloroacetyl chloride at which point additional dichloromethane (100 mL) was added. The reaction was stirred for 1 hour at ambient temperature. The yellow suspension was quenched first with aqueous saturated sodium bicarbonate followed by 50% aqueous sodium hydroxide until a pH of 14 was reached. Filtration provided 10 g of N-{7-bromo-4-[(tetrahydro-2H-pyran-4-ylmethyl)amino]quinolin-3-yl}-2-chloroacetamide as a tan solid. The filtrate was placed in a separatory funnel and the layers were separated. The aqueous layer was extracted with additional dichloromethane. The combined organic extracts were combined, dried over sodium sulfate, filtered, and concentrated under reduced pressure to afford additional N-{7-bromo-4-[(tetrahydro-2H-pyran-4-ylmethyl)amino]quinolin-3-yl}-2-chloroacetamide as a yellow oil. The yellow oil was carried forward without further purification assuming a 50% yield (27.3 mmol). The oil was combined with ethanol (100 mL) and triethylamine (7.5 mL, 54 mmol). The resulting yellow solution was refluxed for 2 hours. The reaction was cooled to ambient temperature and the solvent was removed under reduced pressure to provide 7-bromo-2-(chloromethyl)-1-(tetrahydro-2H-pyran-4-ylmethyl)-1H-imidazo[4,5-c]quinoline as a brown oil that was used without further purification assuming quantitative yield.

Part D

Potassium acetate (5.3 g, 55 mmol) was added to 7-bromo-2-(chloromethyl)-1-(tetrahydro-2H-pyran-4-ylmethyl)-1H-imidazo[4,5-c]quinoline (27.3 mmol) dissolved in dimethylformamide (100 mL). The resulting suspension was stirred at 90° C. for 1 hour. The reaction was cooled to ambient temperature and water (200 mL) was added. The aqueous layer was extracted with chloroform. The combined organic extracts were combined, dried over sodium sulfate, filtered, and concentrated under reduced pressure to afford an orange oily solid. Chromatography (SiO$_2$, 0-30% 80/18/2 v/v/v CHCl$_3$/CH$_3$OH/concentrated NH$_4$OH (CMA)/CHCl$_3$) gave material that was stirred in acetonitrile and filtered to provide 2.3 g of [7-bromo-1-(tetrahydro-2H-pyran-4-ylmethyl)-1H-imidazo[4,5-c]quinolin-2-yl]methyl acetate as a tan solid.

Part E

3-Chloroperoxybenozic acid (2.4 g, 50% pure, 7.0 mmol) was added to a mixture of [7-bromo-1-(tetrahydro-2H-pyran-4-ylmethyl)-1H-imidazo[4,5-c]quinolin-2-yl]methyl acetate (2.3 g, 5.4 mmol) and chloroform (27 mL) at ambient temperature. The reaction was stirred at this temperature for 18 hours. Saturated aqueous sodium bicarbonate (50 mL) and water (50 mL) were then added to the reaction and the layers were separated. The aqueous layer was extracted with additional dichloromethane. The organic layers were combined, dried over sodium sulfate, and concentrated under reduced pressure to a dark oil. This oil was dissolved in methanol (27 mL) and to this solution was added 15 M ammonium hydroxide (3.6 mL, 54 mmol) and benzene sulfonyl chloride (2.9 mL, 23 mmol). The resulting reaction mixture was stirred at ambient temperature for 2 hours before adding additional 15 M ammonium hydroxide (3.6 mL, 54 mmol) and benzene sulfonyl chloride (2.9 mL, 23 mmol). The reaction was stirred 18 hours. The reaction was then concentrated under reduced pressure and diluted with saturated aqueous sodium bicarbonate and chloroform. A suspension resulted that was filtered to afford a solid that was stirred with saturated aqueous sodium bicarbonate and filtered to give 1.1 g of [4-amino-7-bromo-1-(tetrahydro-2H-pyran-4-ylmethyl)-1H-imidazo[4,5-c]quinolin-2-yl]methanol as a white solid.

Part F

To a mixture of [4-amino-7-bromo-1-(tetrahydro-2H-pyran-4-ylmethyl)-1H-imidazo[4,5-c]quinolin-2-yl]methanol (500 mg, 1.28 mmol), 3-pyridyl boronic acid (233 mg, 1.90 mmol), potassium carbonate (579 mg, 4.20 mmol), dimethoxyethane (5 mL), and water (2.5 mL) under a nitrogen atmosphere was added Pd(PPh$_3$)$_2$Cl$_2$ (18 mg, 0.026 mmol). The resulting suspension was refluxed for 2 hours. The reaction was cooled to ambient temperature. The reaction mixture was diluted with chloroform and placed directly onto a silica gel column. Chromatography (SiO$_2$, 0-40% CMA/CHCl$_3$) gave material that was stirred in methanol and filtered to provide 263 mg of [4-amino-7-pyridin-3-yl-1-(tetrahydro-2H-pyran-4-ylmethyl)-1H-imidazo[4,5-c]quinolin-2-yl]methanol as tan crystals, m.p. 260-262° C. MS (APCI) m/z 500.3 (M+H)$^+$; Anal. calcd for C$_{22}$H$_{23}$N$_5$O$_2$: C, 67.85; H, 5.95; N, 17.98. Found: C, 67.49; H, 5.87; N, 17.83.

Examples 33-44

The compounds in the table below were prepared according to the following general procedure. The ether analog was dissolved or suspended in a solvent such as dichloromethane and the reaction mixture was stirred at 0° C. or at ambient temperature. Boron tribromide (2.5-10 equivalents, 1 M solution in dichloromethane) was added dropwise to the reaction mixture. The reaction was stirred at ambient temperature for 4 h-6 days after which it was quenched by the careful addition of methanol or water and the solvent was removed under reduced pressure. The product was isolated by a procedure similar to that described below. The residue was combined with 2-6 M hydrochloric acid, heated to 50° C., and stirred for 1-2 hours. The resulting solution was cooled (ice bath) and then free-based (pH 9) with the addition of 2-6 M aqueous sodium hydroxide. The desired material was extracted from the aqueous using an organic solvent such as dichloromethane, ethyl acetate, or chloroform. The organic layer was separated, dried (MgSO4), filtered, and the solvent was evaporated under reduced pressure to afford the crude product. The final compound was isolated by prep HPLC (ISCO Combiflash Separation System or Analogix Purification System).

| Example | Structure | Analytical Data |
|---|---|---|
| 33 | 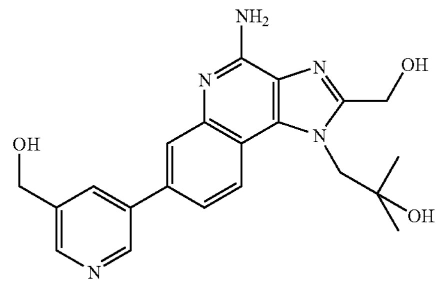 | Off-white needles, mp 180-182° C. Anal. calcd for $C_{21}H_{23}N_5O_3 \cdot 2.60H_2O$: C, 57.29; H, 6.46; N, 15.91. Found: C, 57.32; H, 6.15; N, 15.73; MS (APCI) m/z 394 $(M + H)^+$. |
| 34 | 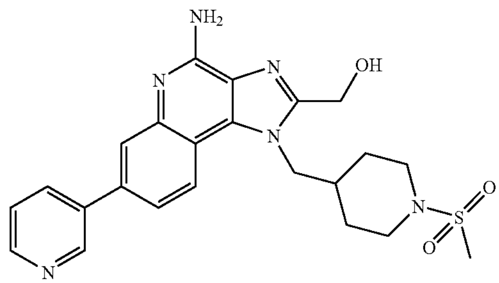 | Off-white needles, mp 196-198° C. Anal. calcd for $C_{23}H_{26}N_6O_3S$: C, 59.21; H, 5.62; N, 18.01. Found: C, 59.16; H, 5.84; N, 17.98; MS (APCI) m/z 467 $(M + H)^+$. |
| 35 | 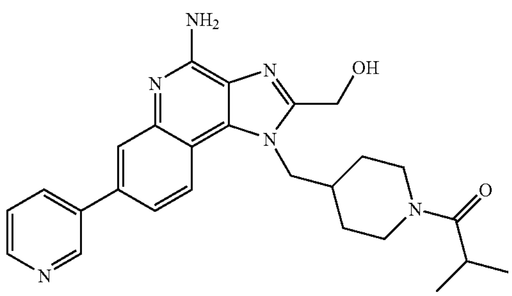 | Off-white needles, mp 154-157° C. Anal. calcd for $C_{26}H_{30}N_6O_2 \cdot 0.25H_2O$: C, 67.44; H, 6.64; N, 18.15. Found: C, 67.48; H, 6.55; N, 18.00; MS (APCI) m/z 459 $(M + H)^+$. |
| 36 | 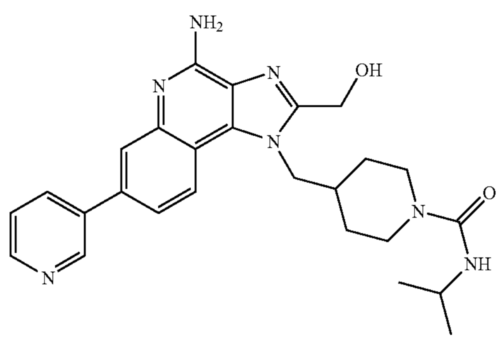 | Off-white needles, mp 182-184° C. Anal. calcd for $C_{26}H_{31}N_7O_2$: C, 65.94; H, 6.60; N, 20.70. Found: C, 65.70; H, 6.49; N, 20.39); MS (APCI) m/z 474 $(M + H)^+$. |
| 37 | 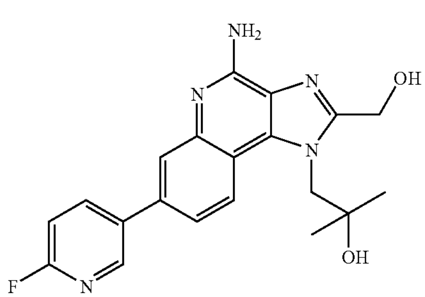 | Beige needles, mp 111-114° C. Anal. calcd for $C_{20}H_{20}FN_5O_2 \cdot 2.0 H_2O$: C, 57.55; H, 5.79; N, 16.78. Found: C, 57.33; H, 5.57; N, 16.76 MS (APCI) m/z 382 $(M + H)^+$ |

-continued

| Example | Structure | Analytical Data |
|---|---|---|
| 38 | 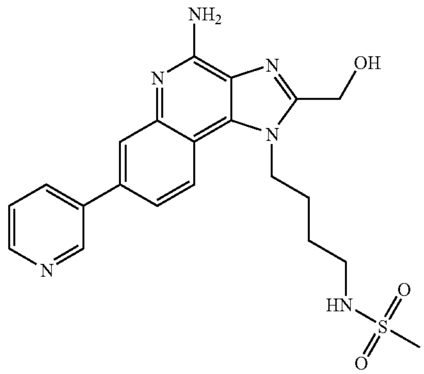 | Off-white solid, mp 188-190° C.<br>Anal. calcd for $C_{21}H_{24}N_6O_3S \cdot 1.70H_2O$<br>C: 53.53, H: 5.86, N: 17.84. Found:<br>C: 53.23, % H: 5.62, N: 17.81.<br>MS (APCI) m/z 459 $(M + H)^+$ |
| 39 | 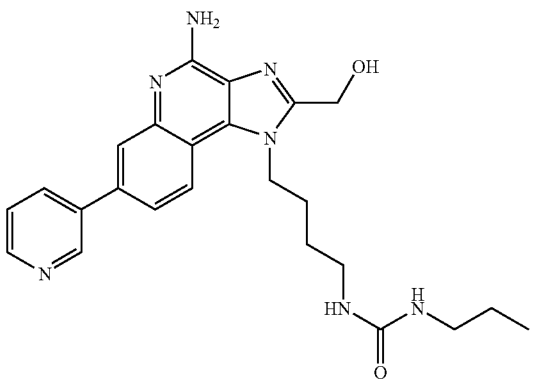 | Green solid, mp 206-209° C.<br>Anal. calcd for $C_{24}H_{29}N_7O_2 \cdot 0.27H_2O$<br>C: 63.72, H: 6.58, N: 21.67.<br>Found: C: 63.97, H: 6.26, N: 21.64.<br>MS (APCI) m/z 448 $(M + H)^+$ |
| 40 | 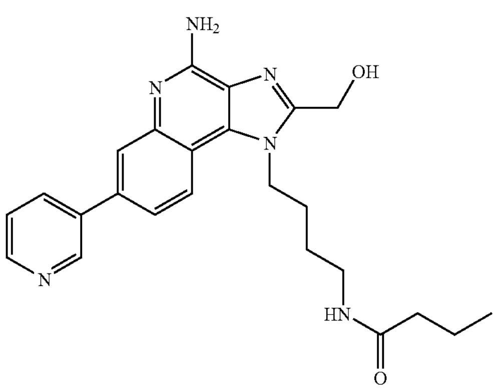 | Off-white solid, mp 211-212° C.<br>Anal. calcd for $C_{24}H_{25}N_6O_2 \cdot 0.25H_2O$<br>C: 65.96, H: 6.57, N: 19.23. Found: C: 65.52<br>H: 6.38, N: 19.38<br>MS (APCI) m/z 433 $(M + H)^+$ |
| 41 | 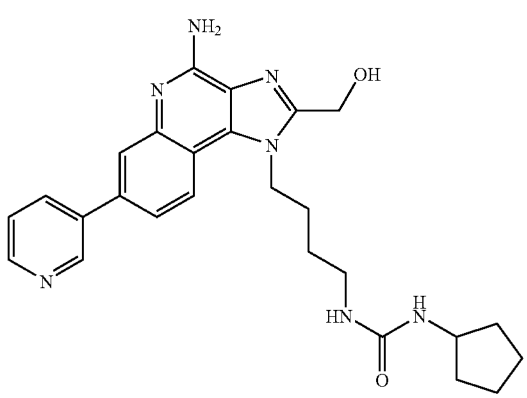 | Yellow solid, mp 225-227° C.<br>Anal. calcd for $C_{26}H_{31}N_7O_2 \cdot 0.38H_2O$<br>C: 65.00, H: 6.66, N: 20.41.<br>Found: C: 65.26, H: 6.53, N: 20.42.<br>MS (APCI) m/z 474 $(M + H)^+$ |

| Example | Structure | Analytical Data |
|---|---|---|
| 42 | 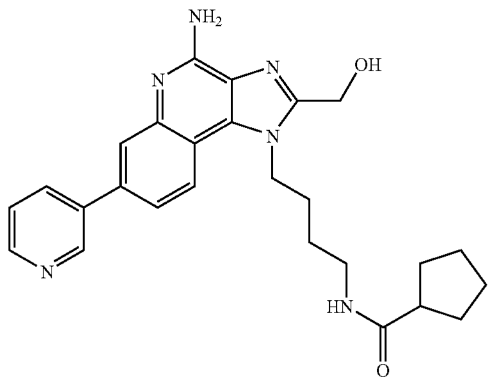 | White solid, mp 241-242° C.<br>Anal. calcd for $C_{26}H_{30}N_6O_2$<br>C: 68.10, H: 6.59, N: 18.33.<br>Found: C: 67.85, H: 6.48, N: 18.32.<br>MS (APCI) m/z 459 (M + H)$^+$ |
| 43 | 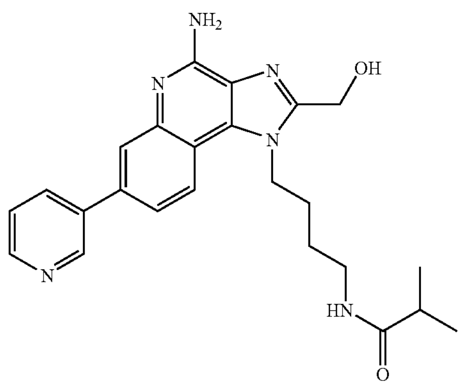 | White solid, mp 225-227° C.<br>Anal. calcd for $C_{24}H_{28}N_6O_2 \cdot 0.38H_2O$<br>C: 65.61, H: 6.60, N: 19.13.<br>Found: C: 65.19, H: 6.74, N: 18.96.<br>MS (APCI) m/z 433 (M + H)$^+$ |
| 44 | 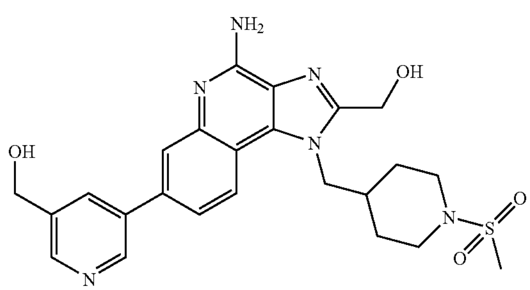 | White solid, mp >300° C.<br>Anal. calcd for $C_{24}H_{28}N_6O_4S \cdot HBr \cdot 0.2H_2O$:<br>C, 49.61; H, 5.10; N, 14.46. Found: C,<br>49.26; H, 4.84; N, 14.29<br>MS (APCI) m/z 497 (M + H)$^+$ |
| 45 | 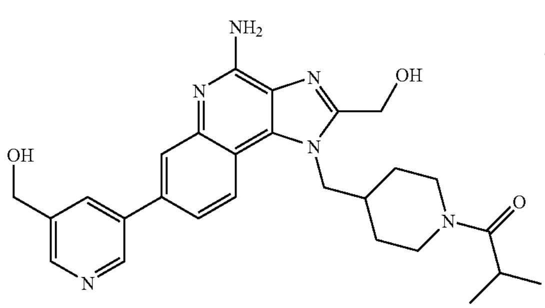 | Tan solid, mp >300° C.<br>Anal. calcd for $C_{27}H_{32}N_6O_3 \cdot HBr$: C, 56.94;<br>H, 5.84; N, 14.76. Found: C, 56.66; H,<br>5.69; N, 14.63.<br>MS (APCI) m/z 489 (M + H)$^+$ |

| Example | Structure | Analytical Data |
|---|---|---|
| 46 | 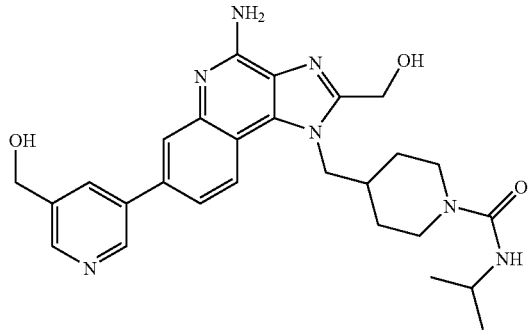 | Off-white solid, mp >300° C.<br>Anal. calcd for $C_{27}H_{33}N_7O_3 \cdot HBr$: C, 55.14; H, 5.90; N, 16.67. Found: C, 54.86; H, 5.60; N, 16.64.<br>MS (APCI) m/z 504 (M + H)$^+$ |
| 47 | 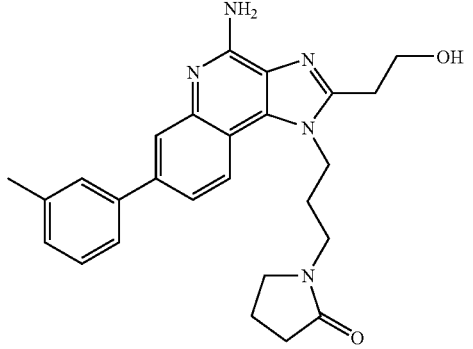 | Off white needles, mp 218-221° C.<br>Anal. calcd for $C_{26}H_{29}N_5O_2 \cdot 1.25\ H_2O$: C, 67.00; H, 6.81; N, 15.03. Found: C, 67.04; H, 6.78, N, 14.90.<br>MS (APCI) m/z 444 (M + H)$^+$ |
| 48 | 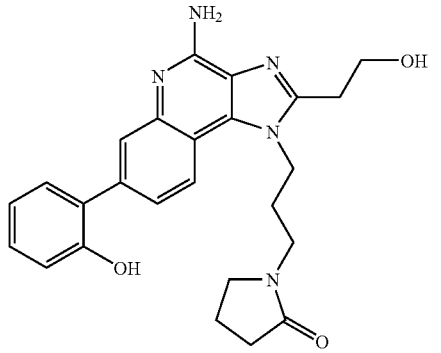 | Off white solid, mp >250° C.<br>Anal. calcd for $C_{25}H_{27}N_5O_3 \cdot 0.75\ H_2O$: C, 65.41; H, 6.26; N, 15.26. Found: C, 65.48; H, 6.40; N, 15.07.<br>MS (APCI) m/z 446 (M + H)$^+$ |

| Example | Structure | Analytical Data |
|---|---|---|
| 49 | 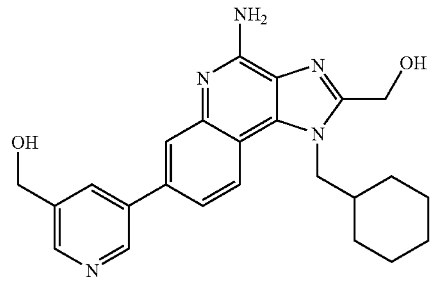 | Off-white solid, mp 166-170° C.<br>Anal. calcd for $C_{24}H_{27}N_5O_2 \cdot 0.9\, H_2O$: C, 66.46; H, 6.69; N, 16.15. Found: C, 66.09; H, 6.73; N, 15.97.<br>MS (APCI) m/z 418 (M + H)$^+$ |
| 50 | 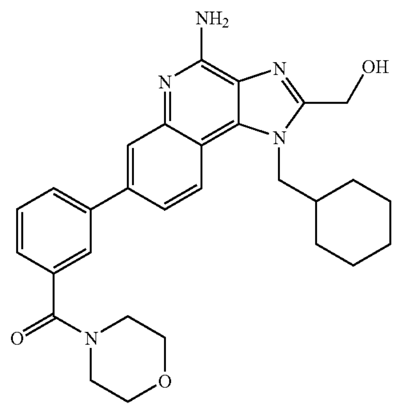 | Off-white solid, mp 260-264° C.<br>Anal. calcd for $C_{29}H_{33}N_5O_3 \cdot 0.6\, H_2O \cdot 1.0$ HCl: C, 63.69; H, 6.49; N, 12.81. Found: C, 63.37; H, 6.23; N, 12.62.<br>MS (APCI) m/z 500.3 (M + H)$^+$ |
| 51 | 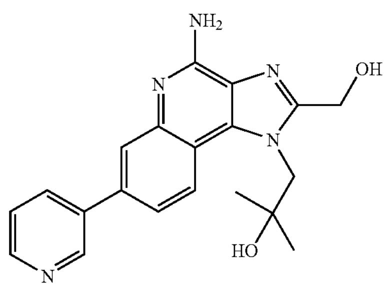 | Off-white needles, mp 141-143° C.<br>Anal. calcd for $C_{20}H_{21}N_5O_2 \cdot 1.00\, CH_4O \cdot 1.0\, H_2O$: C, 61.15 H, 6.35 N, 16.98. Found: C, 61.15 H, 6.06 N, 17.34.<br>MS (APCI) m/z 364 (M + H)$^+$ |

Examples 52-92

Part A

A solution of 1-(4-aminobutyl)-2-ethoxymethyl-7-(pyridin-3-yl)-1H-imidazo[4,5-c]quinoline-4-amine (43 mg, 0.10 mmol, 1 eq, U.S. Patent Application Publication 2004/0147543, Example 372) and triethylamine (5 eq) in chloroform (1 mL) was added to a tube containing a reagent (1.1 eq) from the table below. The reaction mixture was vortexed overnight and then purified by solid-supported liquid-liquid extraction according to the following procedure. The reaction mixture was loaded onto diatomaceous earth that had been equilibrated with 1 N sodium hydroxide (600 μL) for about 20 minutes. After 10 minutes chloroform (300 μL) was added to elute the product from the diatomaceous earth into a well of a collection plate. After an additional 10 minutes the process was repeated with additional chloroform (500 μL). The solvent was then removed by vacuum centrifugation.

Part B

The material from Part A was dissolved in dichloromethane (600 μL) and the solution was cooled to 0° C. Boron tribromide (400 μL of 1 M in dichloromethane) was added, the reaction mixture was vortexed, chilled for 15 minutes, and then vortexed at ambient temperature overnight. The solvent was removed by vacuum centrifugation. Methanol (300 μL) and 6 N hydrochloric acid (300 μL) were added and the reaction mixture was vortexed for 10 minutes. The solvent was removed by vacuum centrifugation. The compounds were purified as described above for Examples 1-6. The table below shows the reagent used for each example, the structure of the resulting compound, and the observed accurate mass for the isolated trifluoroacetate salt.

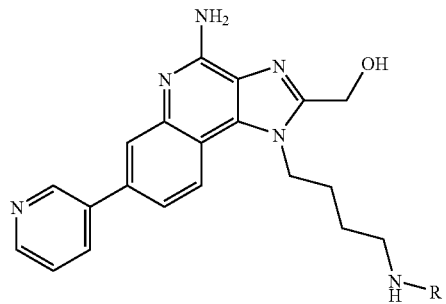

| Example | Reagent | R | Measured Mass (M + H) |
|---|---|---|---|
| 52 | None | —H | 363.1964 |
| 53 | Propionyl chloride | (acetyl with CH₃) | 419.2168 |
| 54 | Cyclopropanecarbonyl chloride | (cyclopropyl carbonyl) | 431.2213 |
| 55 | Butyryl chloride | (propyl carbonyl) | 433.2345 |
| 56 | Isobutyryl chloride | (isopropyl carbonyl) | 433.2346 |
| 57 | Methoxyacetyl chloride | (CH₂OH carbonyl) | 421.1982 |
| 58 | Cyclobutanecarbonyl chloride | (cyclobutyl carbonyl) | 445.2338 |
| 59 | Isovaleryl chloride | (isobutyl carbonyl) | 447.2536 |
| 60 | Cyclohexanecarbonyl chloride | (cyclohexyl carbonyl) | 473.2679 |

-continued
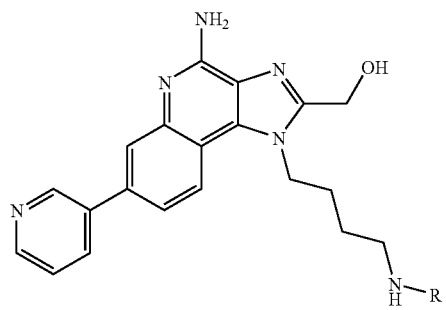
| Example | Reagent | R | Measured Mass (M + H) |
|---|---|---|---|
| 61 | Phenylacetyl chloride | 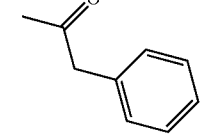 | 481.2368 |
| 62 | 4-Cyanobenzoyl chloride | 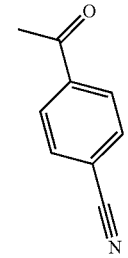 | 492.2143 |
| 63 | 3-Methoxybenzoyl chloride | 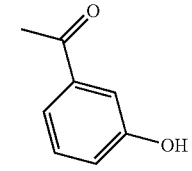 | 483.2121 |
| 64 | p-Anisoyl chloride | 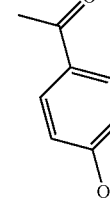 | 483.2115 |
| 65 | 2-Chlorobenzoyl chloride | 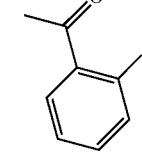 | 501.1813 |
| 66 | 3-Chlorobenzoyl chloride | 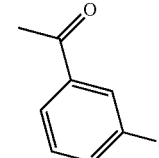 | 501.1812 |

-continued
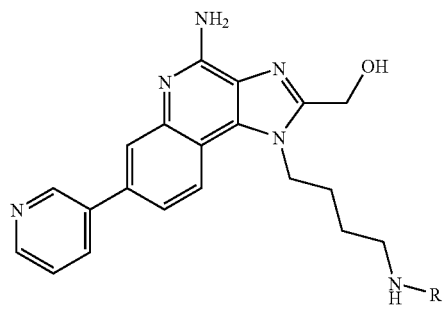
| Example | Reagent | R | Measured Mass (M + H) |
|---|---|---|---|
| 67 | Nicotinoyl chloride hydrochloride | 3-pyridyl C(=O)– | 468.2122 |
| 68 | Picolinoyl chloride hydrochloride | 2-pyridyl C(=O)– | 468.2124 |
| 69 | 1-Propanesulfonyl chloride | CH₃CH₂CH₂SO₂– | 469.2039 |
| 70 | Dimethylsulfamoyl chloride | (CH₃)₂NSO₂– | 470.1961 |
| 71 | 1-Butanesulfonyl chloride | CH₃CH₂CH₂CH₂SO₂– | 483.2160 |
| 72 | 3-Methylbenzenesulfonyl chloride | 3-methylphenyl SO₂– | 517.2044 |

-continued
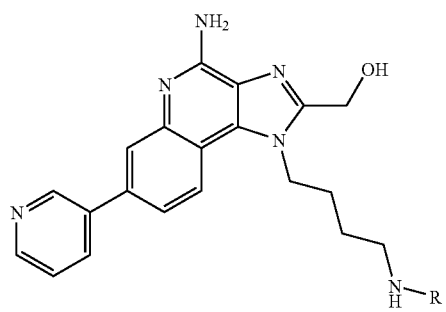
| Example | Reagent | R | Measured Mass (M + H) |
|---|---|---|---|
| 73 | o-Toluenesulfonyl chloride | 2-methylphenyl sulfonyl | 517.2071 |
| 74 | p-Toluenesulfonyl chloride | 4-methylphenyl sulfonyl | 517.2020 |
| 75 | 2-Fluorobenzenesulfonyl chloride | 2-fluorophenyl sulfonyl | 521.1786 |
| 76 | 3-Cyanobenzenesulfonyl chloride | 3-cyanophenyl sulfonyl | 528.1805 |
| 77 | 3-Methoxybenzenesulfonyl chloride | 3-hydroxyphenyl sulfonyl | 519.1829 |

-continued
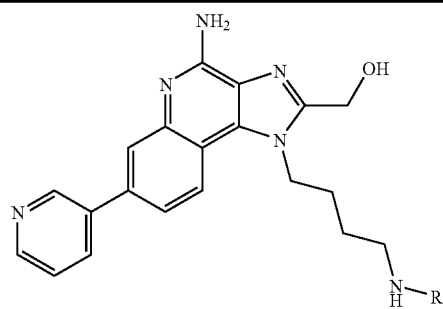
| Example | Reagent | R | Measured Mass (M + H) |
|---|---|---|---|
| 78 | 4-Methoxybenzenesulfonyl chloride | sulfonyl-phenyl-OH | 519.1799 |
| 79 | 3-Pyridinesulfonyl chloride hydrochloride | sulfonyl-pyridin-3-yl | 504.1852 |
| 80 | Ethyl isocyanate | C(O)NH-CH₂CH₃ | 434.2307 |
| 81 | Isopropyl isocyanate | C(O)NH-CH(CH₃)₂ | 448.2498 |
| 82 | n-Propyl isocyanate | C(O)NH-CH₂CH₂CH₃ | 448.2448 |
| 83 | Cyclopentyl isocyanate | C(O)NH-cyclopentyl | 474.2629 |
| 84 | Phenyl isocyanate | C(O)NH-phenyl | 482.2338 |

-continued
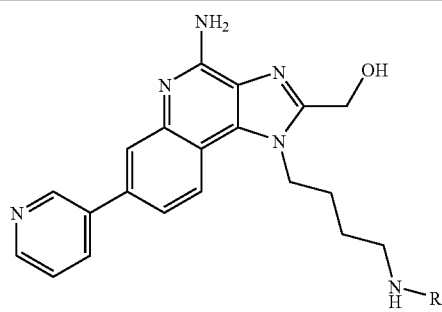
| Example | Reagent | R | Measured Mass (M + H) |
|---|---|---|---|
| 85 | Cyclohexyl isocyanate | -C(O)NH-cyclohexyl | 488.2759 |
| 86 | 2-Fluorophenyl isocyanate | -C(O)NH-(2-F-C6H4) | 500.2209 |
| 87 | 3-Fluorophenyl isocyanate | -C(O)NH-(3-F-C6H4) | 500.2206 |
| 88 | 4-Fluorophenyl isocyanate | -C(O)NH-(4-F-C6H4) | 500.2209 |
| 89 | (R)-(+)-alpha-Methylbenzyl isocyanate | -C(O)NH-CH(CH3)-Ph (R) | 510.2580 |
| 90 | (S)-(-)-alpha-Methylbenzyl isocyante | -C(O)NH-CH(CH3)-Ph (S) | 510.2588 |

-continued

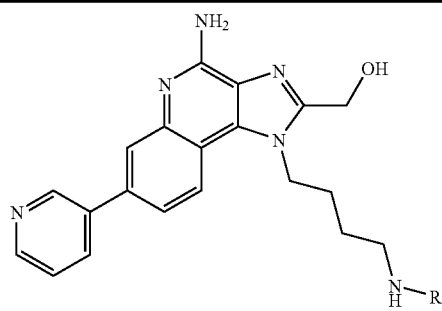

| Example | Reagent | R | Measured Mass (M + H) |
|---|---|---|---|
| 91 | 1-Piperidinecarbonyl chloride | (acetyl-piperidine structure) | 474.2606 |
| 92 | 4-Methyl-1-piperazinecarbonyl chloride | (acetyl-4-methylpiperazine structure) | 489.2725 |

Examples 93-119

The compounds in the table below were prepared and purified according to the general method of Examples 7-31 using N-{4-[4-amino-7-bromo-2-ethoxymethyl-1H-imidazo[4,5-c]quinolin-1-yl]butyl}methanesulfonamide (U.S. Patent Application Publication 2004/0147543, Example 612) in lieu of 1-(4-amino-7-bromo-2-ethoxymethyl-1H-imidazo[4,5-c]quinolin-1-yl)-2-methylpropan-2-ol. Prior to purification by solid phase extraction, the reaction mixture for Example 119 was combined with water (500 μL), glacial acetic acid (500 μL), and tetrahydrofuran (500 μL) and then heated at 60° C. for 2 hours. The table below shows the boronic acid, the structure of the resulting compound, and the observed accurate mass for the isolated trifluoroacetate salt.

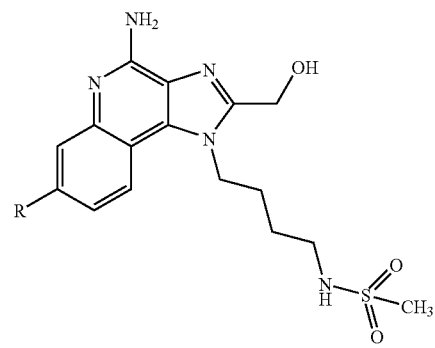

| Example | Reagent | R | Measured Mass (M + H) |
|---|---|---|---|
| 93 | Phenylboronic acid | (phenyl) | 440.1745 |

-continued

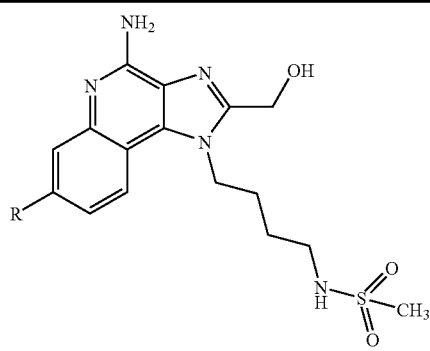

| Example | Reagent | R | Measured Mass (M + H) |
|---|---|---|---|
| 94 | Pyridine-3-boronic acid | 3-pyridyl | 441.1745 |
| 95 | Pyridine-4-boronic acid | 4-pyridyl | 441.1679 |
| 96 | Thiophene-3-boronic acid | 3-thienyl | 446.1307 |
| 97 | 2-Fluorophenylboronic acid | 2-fluorophenyl | 458.1668 |
| 98 | 3-Fluorophenylboronic acid | 3-fluorophenyl | 458.1671 |
| 99 | 4-Fluorophenylboronic acid | 4-fluorophenyl | 458.1674 |
| 100 | 4-Cyanophenylboronic acid | 4-cyanophenyl | 465.1684 |
| 101 | 3-(Hydroxymethyl)phenylboronic acid | 3-(hydroxymethyl)phenyl | 470.1882 |
| 102 | 4-(Hydroxymethyl)phenylboronic acid | 4-(hydroxymethyl)phenyl | 470.1909 |

-continued

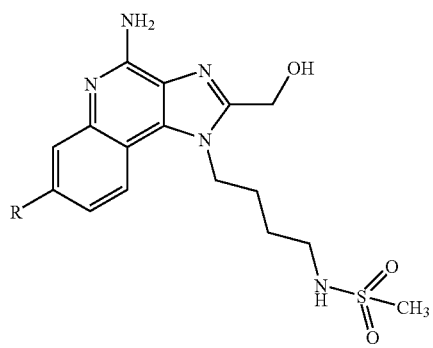

| Example | Reagent | R | Measured Mass (M + H) |
|---|---|---|---|
| 103 | 3-Chlorophenylboronic acid | 3-chlorophenyl | 474.1408 |
| 104 | 2-Chlorophenylboronic acid | 2-chlorophenyl | 474.1366 |
| 105 | 4-Chlorophenylboronic acid | 4-chlorophenyl | 474.1384 |
| 106 | (2-Aminocarbonylphenyl)boronic acid | 2-aminocarbonylphenyl | 483.1796 |
| 107 | (3-Aminocarbonylphenyl)boronic acid | 3-aminocarbonylphenyl | 483.1812 |
| 108 | (2-Acetylaminophenyl)boronic acid | 2-acetylaminophenyl | 497.1938 |
| 109 | [3-(3-Hydroxypropyl)phenyl]boronic acid | 3-(3-hydroxypropyl)phenyl | 498.2136 |

-continued

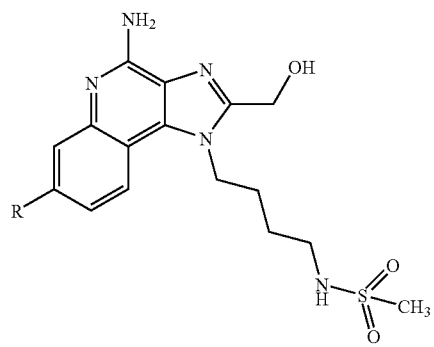

| Example | Reagent | R | Measured Mass (M + H) |
|---|---|---|---|
| 110 | 3,4-Dichlorophenylboronic acid | 3,4-dichlorophenyl | 508.0989 |
| 111 | 3-(N-Isopropylaminocarbonyl)phenylboronic acid | 3-(N-isopropylaminocarbonyl)phenyl | 525.2331 |
| 112 | 3-(N-Propylaminocarbonyl)phenylboronic acid | 3-(N-propylaminocarbonyl)phenyl | 525.2284 |
| 113 | 3-(Methylsulfonylamino)phenylboronic acid | 3-(methylsulfonylamino)phenyl | 533.1659 |
| 114 | 3-(Pyrrolidine-1-carbonyl)phenylboronic acid | 3-(pyrrolidine-1-carbonyl)phenyl | 537.2320 |

-continued

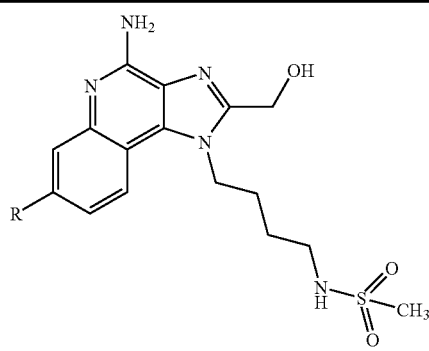

| Example | Reagent | R | Measured Mass (M + H) |
|---|---|---|---|
| 115 | 4-(Pyrrolidine-1-carbonyl)phenylboronic acid | *4-(pyrrolidin-1-ylcarbonyl)phenyl* | 537.2271 |
| 116 | 3-(Isobutylaminocarbonyl)phenylboronic acid | *3-(isobutylaminocarbonyl)phenyl* | 539.2418 |
| 117 | 4-(Isobutylaminocarbonyl)phenylboronic acid | *4-(isobutylaminocarbonyl)phenyl* | 539.2429 |
| 118 | 3-(Piperidine-1-carbonyl)phenylboronic acid | *3-(piperidin-1-ylcarbonyl)phenyl* | 551.2483 |
| 119 | 5-tert-butyldimethylsilanyloxy-methyl)pyridine-3-boronic acid | *5-(hydroxymethyl)pyridin-3-yl* | 471.1819 |

Examples 120-138

The compounds in the table below were prepared according to the following method. A test tube containing a solution of the corresponding ether analog (ethoxymethyl or methoxyethyl) in dichloromethane (1 mL) was cooled to 0° C. in an ice bath. Boron tribromide (4 eq of 1 M in dichloromethane) was added. The tube was vortexed, maintained at 0° C. for 0.5 hr, and then stirred at ambient temperature for 9 hours. Methanol (1 mL) and 6 N hydrochloric acid (500 μL) were added and the tube was vortexed for 5 minutes. The solvent was removed by vacuum centrifugation. The compounds were purified as described above for Examples 1-6. The table below shows a reference for the starting ether, the structure of the resulting compound, and the observed accurate mass for the isolated trifluoroacetate salt.

| Example | U.S. patent application Publication 2004/0147543 | $R_1$ | $R_2$ | $R_3$ | Measured Mass (M + H) |
|---------|---------------------------------------------------|-------|-------|-------|------------------------|
| 120 | Example 102 | isobutyl (CH(CH3)CH2CH3) | CH2CH2OH | phenyl | 347.1904 |
| 121 | Example 111 | isobutyl | CH2CH2OH | 3-cyanophenyl | 372.1819 |
| 122 | Example 201 | C(CH3)2CH2CH2NHS(O)2CH3 | CH2CH2OH | phenyl | 440.1755 |
| 123 | Example 113 | isobutyl | CH2CH2OH | pyridin-3-yl | 348.1810 |
| 124 | Example 194 | 4-(isobutyryl)piperidin-1-ylmethyl | CH2CH2OH | phenyl | 458.2540 |
| 125 | Example 139 | CH2C(CH3)2OH | CH2CH2CH2OH | 3-(methanesulfonamido)phenyl | 470.1832 |
| 126 | Example 152 | CH2CH2CH2CH2-N(isothiazolidine-1,1-dioxide) | CH2CH2OH | phenyl | 466.1897 |

-continued

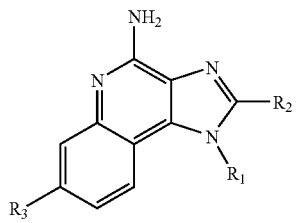

| Example | U.S. patent application Publication 2004/0147543 | R₁ | R₂ | R₃ | Measured Mass (M + H) |
|---|---|---|---|---|---|
| 127 | Example 180 | 4-ethyl-piperidine-1-carbonyl-morpholine | ethanol (OH) | 3-pyridyl | 502.2554 |
| 128 | Example 129 | 2-methyl-2-hydroxybutyl (C(CH₃)₂OH with ethyl) | ethanol (OH) | 3-(pyrrolidine-1-carbonyl)phenyl | 460.2326 |
| 129 | Example 130 | 2-methyl-2-hydroxybutyl | ethanol (OH) | 3-(morpholine-4-carbonyl)phenyl | 476.2285 |
| 130 | Example 185 | 1-butyl-2-oxopyrrolidin-1-yl (N-butyl-pyrrolidinone) | propanol (OH) | 3-(hydroxymethyl)phenyl | 460.2365 |
| 131 | Example 376 | N-pentyl propane-sulfonamide | ethanol (OH) | 3-pyridyl | 469.2024 |
| 132 | Example 438 | 2-cyclohexylethyl | ethanol (OH) | 3-pyridyl | 388.2130 |

-continued

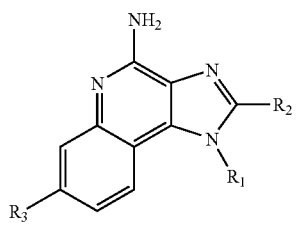

| Example | U.S. patent application Publication 2004/0147543 | R₁ | R₂ | R₃ | Measured Mass (M + H) |
|---|---|---|---|---|---|
| 133 | Example 492 | 2-ethylpiperidine with N-SO₂CH₃ | ethyl-OH | 3-pyridyl | 467.1852 |
| 134 | Example 488 | (R)-2,3-dihydroxybutyl | ethyl-OH | 3-pyridyl | 366.1574 |
| 135 | Example 422 | N-(tert-pentyl) isobutyramide | ethyl-OH | 3-pyridyl | 433.2374 |
| 136 | Example 480 | (tetrahydropyran-4-yl)ethyl | ethyl-OH | 3-(methanesulfonamido)phenyl | 482.1815 |
| 137 | * | pentyl-NH-C(O)-morpholine | ethyl-OH | 3-pyridyl | 476.2383 |
| 138 | Example 670 | 4-(2-oxopyrrolidin-1-yl)butyl | propyl-OH | 3,5-dimethylphenyl | 444.2371 |

*Although not specifically exemplified, the compound is readily prepared using the disclosed synthetic methods.

Example 139

[4-Amino-7-[3-(pyrrolidin-1-ylcarbonyl)phenyl]-1-(tetrahydro-2H-pyran-4-ylmethyl)-1H-imidazo[4,5-c]quinolin-2-yl]methanol

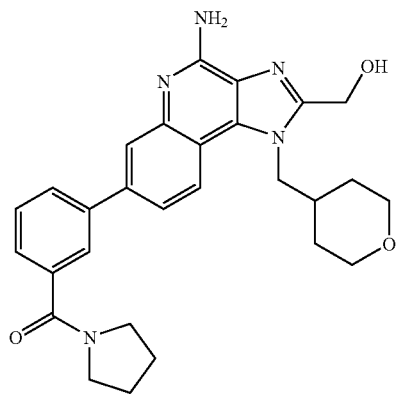

To a mixture of [4-amino-7-bromo-1-(tetrahydro-2H-pyran-4-ylmethyl)-1H-imidazo[4,5-c]quinolin-2-yl]methanol (400 mg, 1.00 mmol), 3-pyrrolidinylcarbonyl phenyl boronic acid (328 mg, 1.50 mmol), potassium carbonate (455 mg, 3.30 mmol), dimethoxyethane (4 mL), and water (2 mL) under a nitrogen atmosphere was added Pd(PPh$_3$)$_2$Cl$_2$ (14 mg, 0.02 mmol). The resulting suspension was refluxed for 18 hours. The reaction was cooled to ambient temperature. The reaction mixture was diluted with water and extracted with chloroform. The organic layer was dried over sodium sulfate, filtered and concentrated under reduced pressure. Chromatography (SiO$_2$, 0-40% CMA/CHCl$_3$) gave material that was stirred in acetonitrile and filtered to provide 100 mg of [4-amino-7-[3-(pyrrolidin-1-ylcarbonyl)phenyl]-1-(tetrahydro-2H-pyran-4-ylmethyl)-1H-imidazo[4,5-c]quinolin-2-yl]methanol as a white powder, m.p. 281-284° C. MS (APCI) m/z 486.3 (M+H)$^+$; Anal. calcd for C$_{28}$H$_{31}$N$_5$O$_3$: C, 69.26; H, 6.43; N, 14.42. Found: C, 68.99; H, 6.16; N, 14.46.

Exemplary Compounds

Certain exemplary compounds, including some of those described above in the Examples, have the following Formulas Ib, Ic, Id, Ie, If, Ig, Ih, Ii, or Ij and the following substituents n and R$_1$ wherein each line of the table is matched to Formula Ib, Ic, Id, Ie, If, Ig, Ih, Ii, or Ij to represent a specific embodiment of the invention.

Ib
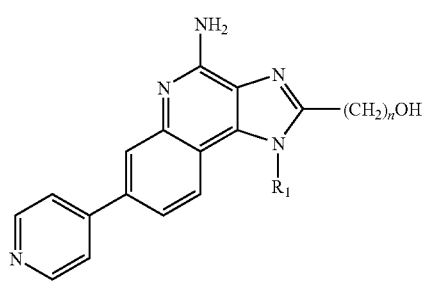

Ic
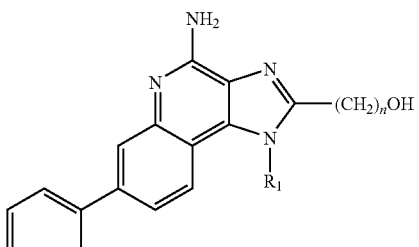

Id
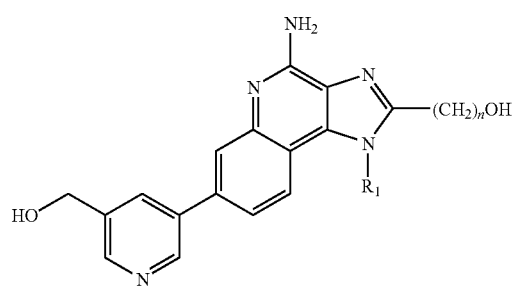

Ie
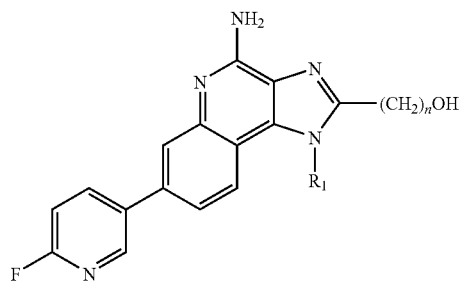

If
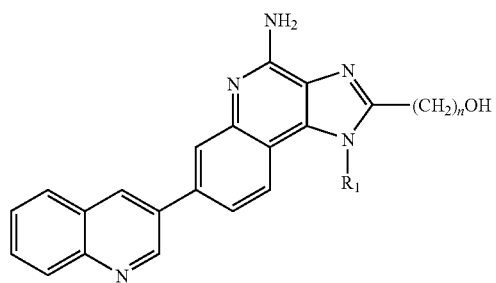

Ig
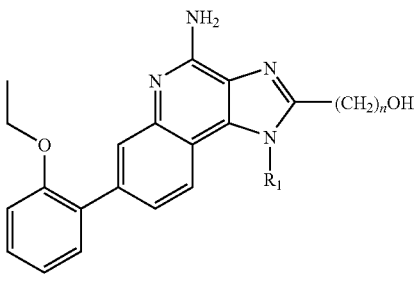

-continued

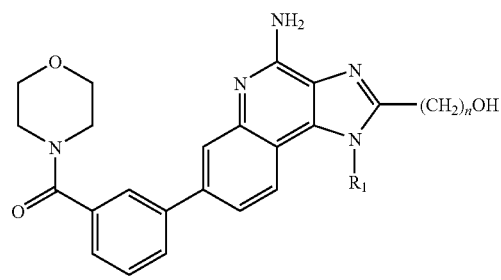

Ih

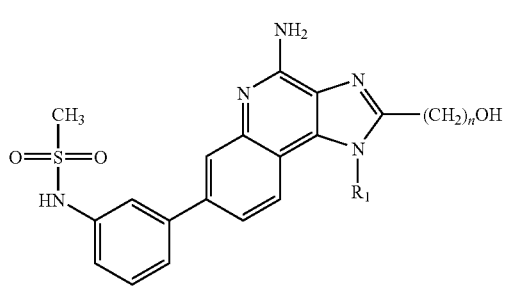

Ii

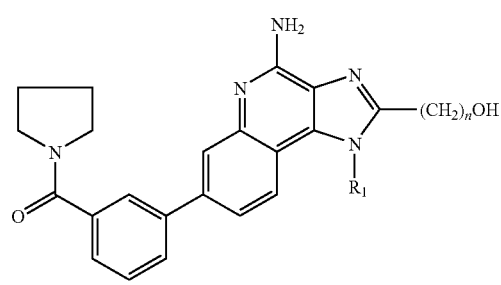

Ij

| n | R₁ |
|---|---|
| 1 | 2-[(cyclohexylcarbonyl)amino]-2-methylpropyl |
| 1 | 2-[(cyclopropylcarbonyl)amino]ethyl |
| 1 | 4-[(cyclopropylcarbonyl)amino]butyl |
| 1 | 2,3-dihydroxypropyl |
| 1 | 2,2-dimethyl-3-(methylsulfonyl)propyl |
| 1 | 2-fluoro-2-methylpropyl |
| 1 | 2-hydroxy-2-methylpropyl |
| 1 | 2-methylpropyl |
| 1 | 2-methyl-2-({[(1-methylethyl)amino]carbonyl}amino)propyl |
| 1 | 2-{[(1-methylethyl)carbonyl]amino}ethyl |
| 1 | 4-{[(1-methylethyl)carbonyl]amino}butyl |
| 1 | 2-methyl-2-[(methylsulfonyl)amino]propyl |
| 1 | 4-[(methylsulfonyl)amino]butyl |
| 1 | 2-[(methylsulfonyl)amino]ethyl |
| 1 | 4-[(4-morpholinecarbonyl)amino]butyl |
| 1 | 2-[(4-morpholinecarbonyl)amino]ethyl |
| 1 | tetrahydro-2H-pyran-4-ylmethyl |
| 1 | (4-hydroxytetrahydro-2H-pyran-4-yl)methyl |
| 1 | (1-hydroxycyclobutyl)methyl |
| 1 | (1-hydroxycyclopentyl)methyl |
| 1 | (1-hydroxycyclohexyl)methyl |
| 2 | 2-[(cyclohexylcarbonyl)amino]-2-methylpropyl |
| 2 | 2-[(cyclopropylcarbonyl)amino]ethyl |
| 2 | 4-[(cyclopropylcarbonyl)amino]butyl |
| 2 | 2,3-dihydroxypropyl |
| 2 | 2,2-dimethyl-3-(methylsulfonyl)propyl |
| 2 | 2-fluoro-2-methylpropyl |
| 2 | 2-hydroxy-2-methylpropyl |
| 2 | 2-methylpropyl |
| 2 | 2-methyl-2-({[(1-methylethyl)amino]carbonyl}amino)propyl |
| 2 | 2-{[(1-methylethyl)carbonyl]amino}ethyl |
| 2 | 4-{[(1-methylethyl)carbonyl]amino}butyl |
| 2 | 2-methyl-2-[(methylsulfonyl)amino]propyl |
| 2 | 4-[(methylsulfonyl)amino]butyl |
| 2 | 2-[(methylsulfonyl)amino]ethyl |
| 2 | 4-[(4-morpholinecarbonyl)amino]butyl |
| 2 | 2-[(4-morpholinecarbonyl)amino]ethyl |
| 2 | tetrahydro-2H-pyran-4-ylmethyl |
| 2 | (4-hydroxytetrahydro-2H-pyran-4-yl)methyl |
| 2 | (1-hydroxycyclobutyl)methyl |
| 2 | (1-hydroxycyclopentyl)methyl |
| 2 | (1-hydroxycyclohexyl)methyl |

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", Journal of Leukocyte Biology, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 μM. Controls include cell samples with media only, cell samples with DMSO only (no compound), and cell samples with reference compound.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (usually 30-0.014 μM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α(y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response (pg/mL) is the maximal response attained in the dose response curve.

Compounds of the invention and close analogs were tested for their ability to induce cytokine biosynthesis using the test method described above. The analogs used are shown in the table below.

| Analog | Chemical Name | Reference |
|---|---|---|
| 1 | 1-(4-amino-2-ethyl-7-pyridin-3-yl-1H-imidazo[4,5-c]quinolin-1-yl)-2-methylpropan-2-ol | U.S. Patent Publication 2004/0147543 Example 142 |
| 2 | 1-(4-amino-2-propyl-7-pyridin-3-yl-1H-imidazo[4,5-c]quinolin-1-yl)-2-methylpropan-2-ol | U.S. Patent Publication 2004/0147543 Example 418 |
| 3 | 1-(4-amino-2-ethoxymethyl-7-pyridin-3-yl-1H-imidazo[4,5-c]quinolin-1-yl)-2-methylpropan-2-ol | U.S. Patent Publication 2004/0147543 Example 126 |

Figure 2:
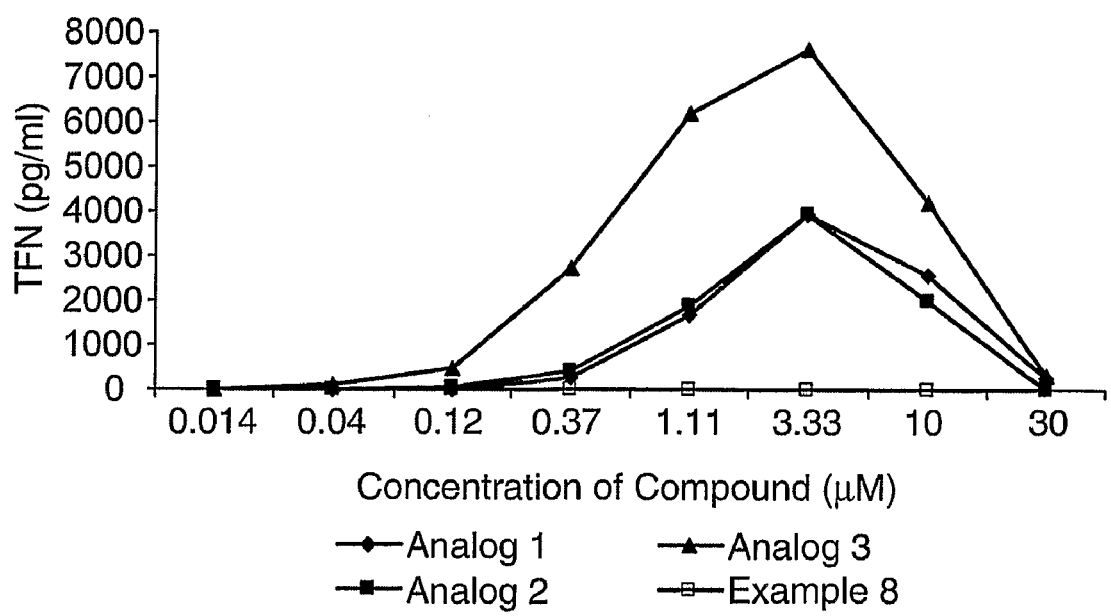
FIG. 2 shows the TNF-α dose response curves (corresponding to values shown in Table 3 below) for Example 8, Analog 1, Analog 2, and Analog 3.

The compound of Example 8 and several closely related analogs were tested using the test method described above. The IFN-α dose response curves are shown in FIG. 1. The TNF-α dose response curves are shown in FIG. 2. The minimum effective concentration for the induction of IFN-α, minimum effective concentration for the induction of TNF-α, the maximal response for IFN-α, and the maximal response for TNF-α are shown in Table 3 below where # is the number of separate experiments in which the compound was tested. When a compound was tested in more than one experiment the values shown are the median values.

TABLE 3

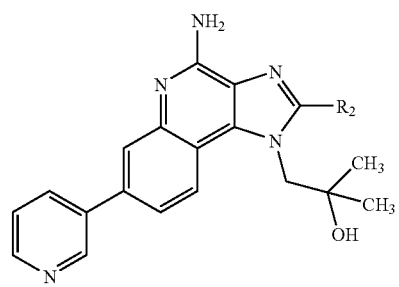

| Compound | $R_2$ | Minimum Effective Concentration (μM) IFN | Minimum Effective Concentration (μM) TNF | Maximal Response (pg/mL) IFN | Maximal Response (pg/mL) TNF | # |
|---|---|---|---|---|---|---|
| Example 8 | —CH$_2$OH | 1.11 | >30 | 2251 | * | 1 |
| Analog 1 | —CH$_2$CH$_3$ | 0.12 | 0.37 | 1118 | 3234 | 4 |
| Analog 2 | —(CH$_2$)$_2$CH$_3$ | 0.04 | 0.37 | 597 | 3951 | 1 |
| Analog 3 | —CH$_2$OCH$_2$CH$_3$ | 0.04 | 0.12 | 840 | 7773 | 5 |

*Below experimental background level of 40/pg mL.

Compounds of the invention and in some instances, close analogs, were tested for their ability to induce cytokine biosynthesis using the test method described above. The minimum effective concentration for the induction of IFN-α, minimum effective concentration for the induction of TNF-α, the maximal response for IFN-α, and the maximal response for TNF-α are shown in the table below where # is the number of separate experiments in which the compound was tested. When a compound was tested in more than one experiment the values shown are the median values.

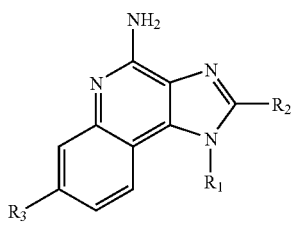

| Compound | R₂ | R₁ | R₃ | Minimum Effective Concentration (μM) IFN | TNF | Maximal Response (pg/mL) IFN | TNF | # |
|---|---|---|---|---|---|---|---|---|
| Example 8 | –CH₂CH₂OH | –C(CH₃)₂CH₂CH₃ (2-methyl-2-hydroxybutyl, i.e. –CH₂C(CH₃)₂OH) | pyridin-3-yl | 0.37 | 10 | 2886 | 51 | 3 |
| Analog 1 | –CH₂CH₃ | –CH₂C(CH₃)₂OH | pyridin-3-yl | 0.12 | 0.37 | 1652 | 3571 | 6 |
| Analog 2 | –CH₂CH₂CH₃ | –CH₂C(CH₃)₂OH | pyridin-3-yl | 0.04 | 0.37 | 597 | 3951 | 1 |
| Analog 3 | –CH₂OCH₂CH₃ | –CH₂C(CH₃)₂OH | pyridin-3-yl | 0.04 | 0.12 | 840 | 7867 | 7 |
| Analog 4 | –CH₂OCH₃ | –CH₂C(CH₃)₂OH | pyridin-3-yl | 0.37 | 1.11 | 829 | 3445 | 4 |
| Analog 5 | –CH₂CH₂OCH₃ | –CH₂C(CH₃)₂OH | pyridin-3-yl | 0.014 | 0.014 | 1065 | 8386 | 8 |
| Example 33 | –CH₂CH₂OH | –CH₂C(CH₃)₂OH | 5-(hydroxymethyl)pyridin-3-yl | 0.37 | >30 | 4357 | * | 3 |
| Analog 6 | –CH₂OCH₃ | –CH₂C(CH₃)₂OH | 5-(hydroxymethyl)pyridin-3-yl | 0.12 | 3.33 | 1771 | 8000 | 4 |
| Analog 7 | –CH₂OCH₂CH₃ | –CH₂C(CH₃)₂OH | 5-(hydroxymethyl)pyridin-3-yl | 0.014 | 0.12 | 6308 | 18284 | 4 |

-continued

[Core structure: 4-amino-imidazoquinoline with R₁ on N1, R₂ at 2-position, R₃ at 7-position]

| Compound | R₂ | R₁ | R₃ | MEC (μM) IFN | MEC (μM) TNF | Max Response (pg/mL) IFN | Max Response (pg/mL) TNF | # |
|---|---|---|---|---|---|---|---|---|
| Analog 8 | -CH₂CH₃ | -CH₂-C(CH₃)₂-OH | (5-methylpyridin-3-yl)methyl-OH | 0.014 | 1.11 | 2084 | 10087 | 5 |
| Analog 9 | -CH₂-O-CH₃ | -CH₂-C(CH₃)₂-OH | (5-methylpyridin-3-yl)methyl-OH | 0.014 | 0.04 | 5868 | 16296 | 2 |
| Analog 10 | -CH₂CH₂CH₃ | -CH₂-C(CH₃)₂-OH | (5-methylpyridin-3-yl)methyl-OH | 0.014 | 0.12 | 1079 | 16482 | 2 |
| Example 35 | -CH₂OH | 4-ethyl-1-(2-methylpropanoyl)piperidin-4-yl | 3-methylpyridinyl | 1.11 | >30 | 969 | * | 1 |
| Analog 11 | -CH₂-O-CH₂CH₃ | 4-ethyl-1-(2-methylpropanoyl)piperidin-4-yl | 3-methylpyridinyl | 0.12 | 0.37 | 2979 | 1449 | 2 |
| Analog 12 | -CH₂CH₃ | 4-ethyl-1-(2-methylpropanoyl)piperidin-4-yl | 3-methylpyridinyl | 0.12 | 1.11 | 1686 | 619 | 8 |
| Analog 13 | -CH₂CH₂CH₃ | 4-ethyl-1-(2-methylpropanoyl)piperidin-4-yl | 3-methylpyridinyl | 0.12 | 0.37 | 1157 | 1054 | 2 |

-continued

[Structure: 4-amino-imidazoquinoline core with substituents R₁ (N1), R₂ (C2), R₃ (7-position)]

| Compound | R₂ | R₁ | R₃ | Minimum Effective Concentration (μM) | | Maximal Response (pg/mL) | | # |
|---|---|---|---|---|---|---|---|---|
| | | | | IFN | TNF | IFN | TNF | |
| Example 1 | propyl-OH | butyl-(pyrrolidin-2-one) | phenyl | >30 | >30 | * | * | 1 |
| Analog 14 | propyl-OCH₃ | butyl-(pyrrolidin-2-one) | phenyl | 0.12 | 1.11 | 1880 | 201 | 2 |
| Analog 15 | ethyl-O-CH₂CH₃ | butyl-(pyrrolidin-2-one) | phenyl | 0.37 | 1.11 | 1665 | 62 | 1 |
| Example 2 | propyl-OH | 2-hydroxy-2-methylbutyl | phenyl | 0.37 | 3.33 | 1274 | 67 | 1 |
| Analog 16 | propyl-OCH₃ | 2-hydroxy-2-methylbutyl | phenyl | 0.014 | 0.014 | 260 | 2296 | 1 |
| Analog 17 | ethyl-O-CH₂CH₃ | 2-hydroxy-2-methylbutyl | phenyl | 0.014 | 0.12 | 440 | 2238 | 1 |
| Example 3 | propyl-OH | sec-butyl (CH(CH₃)CH₂CH₃) | 3-pyridyl | 0.37 | 3.33 | 1180 | 42 | 1 |
| Analog 18 | propyl-OCH₃ | sec-butyl | 3-pyridyl | 0.014 | 0.04 | 1199 | 3151 | 3 |

-continued

Structure: 4-amino-imidazoquinoline core with $R_1$ on N1, $R_2$ on C2, $R_3$ on the benzene ring.

| Compound | $R_2$ | $R_1$ | $R_3$ | Min. Eff. Conc. (μM) IFN | Min. Eff. Conc. (μM) TNF | Max. Response (pg/mL) IFN | Max. Response (pg/mL) TNF | # |
|---|---|---|---|---|---|---|---|---|
| Analog 19 | —CH$_2$—O—CH$_2$CH$_3$ | —CH(CH$_3$)$_2$-isobutyl (CH$_2$CH(CH$_3$)$_2$) | pyridin-3-yl | 0.014 | 0.12 | 591 | 647 | 1 |
| Example 4 | —CH$_2$CH$_2$CH$_2$OH | isobutyl | 5-methylpyridin-3-yl-CH$_2$— (with OH) | 0.12 | 10 | 1891 | 349 | 1 |
| Analog 20 | —CH$_2$CH$_2$CH$_2$—O—CH$_3$ | isobutyl | 5-methylpyridin-3-yl-CH$_2$— (with OH) | 0.014 | 0.04 | 1332 | 9563 | 2 |
| Analog 21 | —CH$_2$—O—CH$_2$CH$_3$ | isobutyl | 5-methylpyridin-3-yl-CH$_2$— (with OH) | 0.04 | 0.37 | 1263 | 3885 | 3 |
| Example 39 | —CH$_2$CH$_2$OH | —(CH$_2$)$_4$—NH—C(O)—NH—CH$_2$CH$_2$CH$_3$ | pyridin-3-yl | 0.37 | 30 | 5089 | 81 | 1 |
| Analog 22 | —CH$_2$—O—CH$_2$CH$_3$ | —(CH$_2$)$_4$—NH—C(O)—NH—CH$_2$CH$_2$CH$_3$ | pyridin-3-yl | 0.04 | 1.11 | 936 | 1059 | 2 |

-continued

| Compound | R₂ | R₁ | R₃ | Minimum Effective Concentration (μM) | | Maximal Response (pg/mL) | | # |
|---|---|---|---|---|---|---|---|---|
| | | | | IFN | TNF | IFN | TNF | |
| Analog 23 | propyl (-CH₂CH₂CH₃) | -(CH₂)₅-NH-C(O)-NH-CH₂CH₂-CH₃ | 3-methylpyridinyl | 0.37 | 0.37 | 531 | 5284 | 1 |
| Analog 40 | -CH₂-OH | -(CH₂)₅-NH-C(O)-NH-CH₂-CH₃ | 3-methylpyridinyl | 0.12 | >30 | 3516 | * | 1 |
| Analog 24 | -CH₂-O-CH₂CH₃ | -(CH₂)₅-NH-C(O)-NH-CH₂-CH₃ | 3-methylpyridinyl | 0.12 | 1.11 | 965 | 991 | 2 |
| Analog 25 | propyl (-CH₂CH₂CH₃) | -(CH₂)₅-NH-C(O)-NH-CH₂-CH₃ | 3-methylpyridinyl | 0.12 | 0.37 | 862 | 1647 | 2 |

-continued

| Compound | R₂ | R₁ | R₃ | Minimum Effective Concentration (μM) | | Maximal Response (pg/mL) | | # |
|---|---|---|---|---|---|---|---|---|
| | | | | IFN | TNF | IFN | TNF | |
| Example 41 | —CH₂OH | —(CH₂)₄—NHC(O)NH-cyclopentyl | 3-pyridyl | 0.04 | 10 | 4373 | 600 | 1 |
| Analog 26 | —CH₂OCH₂CH₃ | —(CH₂)₄—NHC(O)NH-cyclopentyl | 3-pyridyl | 0.014 | 1.11 | 925 | 1618 | 2 |
| Analog 27 | —CH₂CH₂CH₃ | —(CH₂)₄—NHC(O)NH-cyclopentyl | 3-pyridyl | 0.014 | 0.37 | 649 | 9019 | 1 |
| Example 42 | —CH₂OH | —(CH₂)₄—NHC(O)-cyclopentyl | 3-pyridyl | 0.12 | 3.33 | 2745 | 410 | 1 |

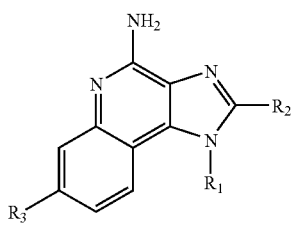
| Compound | R₂ | R₁ | R₃ | Minimum Effective Concentration (μM) | | Maximal Response (pg/mL) | | # |
| --- | --- | --- | --- | --- | --- | --- | --- | --- |
| | | | | IFN | TNF | IFN | TNF | |
| Analog 28 | —CH₂—O—CH₂CH₃ | —(CH₂)₄—NHC(O)-cyclopentyl | 3-pyridyl | 0.04 | 0.37 | 969 | 1366 | 2 |
| Analog 29 | —CH₂CH₂CH₃ | —(CH₂)₄—NHC(O)-cyclopentyl | 3-pyridyl | 0.12 | 0.37 | 521 | 2222 | 1 |
| Example 43 | —CH₂OH | —(CH₂)₄—NHC(O)CH(CH₃)₂ | 3-pyridyl | 0.37 | 10 | 5880 | 217 | 1 |
| Analog 30 | —CH₂—O—CH₂CH₃ | —(CH₂)₄—NHC(O)CH(CH₃)₂ | 3-pyridyl | 0.12 | 1.11 | 1194 | 728 | 2 |

-continued

[Core structure: 4-amino-1H-imidazo[4,5-c]quinoline with R$_2$ at 2-position, R$_1$ on N1, R$_3$ at 7-position]

| Compound | R$_2$ | R$_1$ | R$_3$ | Min. Eff. Conc. (µM) IFN | Min. Eff. Conc. (µM) TNF | Max Response (pg/mL) IFN | Max Response (pg/mL) TNF | # |
|---|---|---|---|---|---|---|---|---|
| Analog 31 | -propyl (CH$_2$CH$_2$CH$_3$) | -(CH$_2$)$_5$-NHC(O)CH(CH$_3$)$_2$ | pyridin-3-yl | 0.12 | 0.37 | 1610 | 960 | 2 |
| Example 5 | -CH$_2$CH$_2$CH$_2$OH | -(CH$_2$)$_4$-(2-oxopyrrolidin-1-yl) | pyridin-3-yl | 30 | >30 | 109 | * | 1 |
| Analog 32 | -CH$_2$CH$_2$CH$_2$OCH$_3$ | -(CH$_2$)$_4$-(2-oxopyrrolidin-1-yl) | pyridin-3-yl | 0.12 | 1.11 | 753 | 380 | 3 |
| Example 6 | -CH$_2$CH$_2$CH$_2$OH | -(CH$_2$)$_4$-(2-oxopyrrolidin-1-yl) | pyridin-4-yl | >30 | >30 | * | * | 1 |
| Analog 33 | -CH$_2$CH$_2$CH$_2$OCH$_3$ | -(CH$_2$)$_4$-(2-oxopyrrolidin-1-yl) | pyridin-4-yl | 0.37 | 3.33 | 1179 | 943 | 3 |
| Example 9 | -CH$_2$CH$_2$OH | -CH$_2$CH$_2$C(CH$_3$)$_2$OH | 3-methylphenyl | 30 | >30 | 87 | * | 1 |

-continued

[Core structure: 4-amino-imidazoquinoline with R₂ at 2-position of imidazole, R₁ on N1, R₃ on benzene ring]

| Compound | R₂ | R₁ | R₃ | Minimum Effective Concentration (μM) IFN | TNF | Maximal Response (pg/mL) IFN | TNF | # |
|---|---|---|---|---|---|---|---|---|
| Analog 34 | −CH₂−O−CH₂CH₃ | −C(CH₃)₂−CH₂OH (2-methyl-2-hydroxybutyl: −CH(CH₂CH₃)... actually −C(CH₃)(CH₃)CH(OH)− see image) | 3,5-dimethylphenyl | 0.014 | 0.12 | 541 | 10184 | 1 |
| Example 10 | −CH₂OH | 2-hydroxy-2-methylbutyl | 4-methylphenyl | 0.37 | 0.37 | 1681 | 7423 | 1 |
| Analog 35 | −CH₂−O−CH₂CH₃ | 2-hydroxy-2-methylbutyl | 4-methylphenyl | 0.12 | 0.12 | 650 | 4456 | 1 |
| Example 13 | −CH₂CH₂OH | 2-hydroxy-2-methylbutyl | 3-hydroxyphenyl | 0.37 | 10 | 12641 | 352 | 1 |
| Analog 36 | −CH₂−O−CH₂CH₃ | 2-hydroxy-2-methylbutyl | 3-hydroxyphenyl | 0.04 | 0.04 | 740 | 3955 | 1 |
| Example 45 | −CH₂CH₂OH | 1-(4-ethylpiperidin-1-yl)-2-methyl-1-oxopropyl (isobutyryl-4-ethylpiperidine linker) | (5-hydroxymethyl)pyridin-3-yl | >30 | >30 | * | * | 1 |

-continued

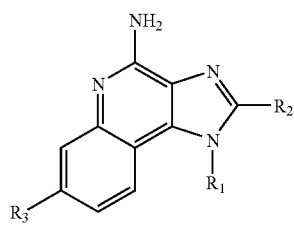

| Compound | R₂ | R₁ | R₃ | Minimum Effective Concentration (μM) | | Maximal Response (pg/mL) | | # |
|---|---|---|---|---|---|---|---|---|
| | | | | IFN | TNF | IFN | TNF | |
| Analog 37 | ethoxymethyl-CH₃ | 4-ethylpiperidine-N-C(O)-CH(CH₃)₂ | 5-methylpyridin-3-yl-CH₂OH | 0.04 | 1.11 | 1382 | 3128 | 1 |
| Example 49 | CH₂OH | cyclohexylmethyl | 5-methylpyridin-3-yl-CH₂OH | 3.33 | >30 | 1087 | * | 1 |
| Analog 38 | ethoxymethyl-CH₃ | cyclohexylmethyl | 5-methylpyridin-3-yl-CH₂OH | 0.014 | 1.11 | 1062 | 2865 | 2 |
| Example 50 | CH₂OH | cyclohexylmethyl | 3-methylphenyl-morpholine amide | 1.11 | >30 | 1266 | * | 1 |
| Analog 39 | ethoxymethyl-CH₃ | cyclohexylmethyl | 3-methylphenyl-morpholine amide | 0.014 | 0.37 | 815 | 1054 | 1 |

*Below experimental background level

All analogs are either specifically exemplified in or are readily prepared using the synthetic methods disclosed in U.S. patent application Publication 2004/0147543

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of Formula I:

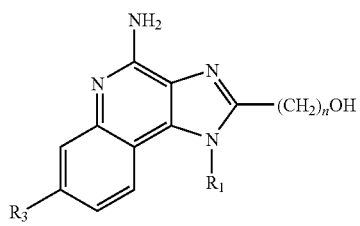

I wherein:
n is 1 or 2;
$R_1$ is selected from the group consisting of:
—$R_4$,
—X—$R_4$,
—X—Y—$R_4$, and
—X—$R_5$;
$R_3$ is selected from the group consisting of:
—Z—Ar,
—Z—Ar'—Y—$R_4$, and
—Z—Ar'—X—Y—$R_4$;
Ar is selected from the group consisting of aryl and heteroaryl both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, amino, alkylamino, and dialkylamino;
Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, amino, alkylamino, and dialkylamino;
X is alkylene optionally interrupted by one —O— group;
Y is selected from the group consisting of:
—O—,
—C($R_6$)—,
—C($R_6$)—N($R_8$)—,
—S(O)$_{0-2}$—,
—N($R_8$)-Q-,

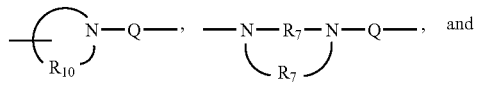

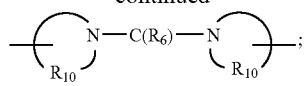

Z is selected from the group consisting of a bond and alkylene;
$R_4$ is selected from the group consisting of hydrogen, alkyl, alkenyl, aryl, arylalkylenyl, heteroaryl, heteroarylalkylenyl, and heterocyclyl, wherein the alkyl, alkenyl, aryl, arylalkylenyl, heteroaryl, heteroarylalkylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and, in the case of alkyl, alkenyl, and heterocyclyl, oxo;
$R_5$ is selected from the group consisting of:

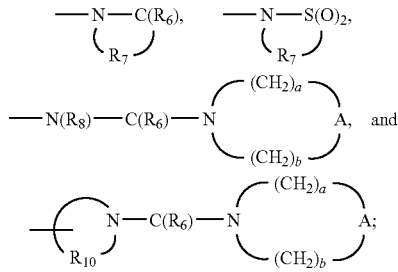

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_{10}$ is $C_{3-8}$ alkylene;
A is selected from the group consisting of —O—, —C(O)—, —CH$_2$—, —S(O)$_{0-2}$—, and —N(Q-$R_4$)—;
Q is selected from the group consisting of a bond, —C($R_6$)—, —S(O)$_2$, —C($R_6$)—N($R_8$)—, —S(O)$_2$—N($R_8$)—, —C($R_6$)—O—, and —C($R_6$)—S—; and
a and b are independently integers from 1 to 6 with the proviso that a+b is ≦7;
or a pharmaceutically acceptable salt thereof.

2. The compound or salt of claim 1 wherein n is 1.

3. The compound or salt of claim 1 wherein $R_1$ is selected from the group consisting of alkyl, aminoalkyl, dihydroxyalkyl, haloalkyl, and hydroxyalkyl.

4. The compound or salt of claim 1 wherein $R_1$ is heterocyclylalkylenyl wherein heterocyclyl is unsubstituted or substituted by one or more substituents independently selected from the group consisting of $C_{1-4}$ alkyl, hydroxy, and oxo.

5. The compound or salt of claim 1 wherein $R_1$ is —X—Y—$R_4$ wherein X is $C_{1-6}$ alkylene which may be interrupted by an —O— group; Y is selected from the group consisting of —N($R_8$)—C(O)—, —N($R_8$)—S(O)$_2$—, —N($R_8$)—C(O)—N($R_8$)—, and —S(O)$_2$— wherein $R_8$ is selected from hydrogen and methyl; and $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl.

6. The compound or salt of claim 1 wherein $R_1$ is —X—Y—$R_4$ wherein X is $C_{1-6}$ alkylene which may be interrupted by an —O— group; Y is selected from the group consisting of —$N(R_8)$—C(O)—, —$N(R_8)$—$S(O)_2$—, —$N(R_8)$—C(O)—$N(R_8)$—, —$N(R_8)$—$S(O)_2$—$N(R_8)$—, —$S(O)_2$—, and

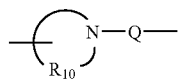

wherein Q is —C(O)—, —C(O)—NH—, or —$S(O)_2$—, $R_{10}$ is pentylene, $R_8$ is hydrogen or methyl; and $R_4$ is selected from the group consisting of $C_{1-6}$ alkyl, hydroxy$C_{1-6}$ alkyl, isoquinolinyl, N-methylimidazolyl, pyridinyl, quinolinyl, benzyl, 1-phenylethyl, phenyl, and phenyl substituted by a substituent selected from the group consisting of chloro, cyano, fluoro, hydroxy, and methyl.

7. The compound or salt of claim 1 wherein Z is a bond.

8. The compound or salt of claim 1 wherein $R_3$ is phenyl, pyridin-2-yl, pyridin-3-yl, pyridin-4-yl, or quinolin-3-yl any of which may be unsubstituted or substituted by one or more substituents selected from the group consisting of alkyl, alkoxy, halogen, hydroxy, and hydroxyalkyl.

9. The compound or salt of claim 1 wherein $R_3$ is thien-3-yl, phenyl, pyridin-2-yl, pyridin-3-yl, pyridin-4-yl, or quinolin-3-yl any of which may be unsubstituted or substituted by one or more substituents selected from the group consisting of alkyl, alkoxy, halogen, cyano, hydroxy, and hydroxyalkyl.

10. The compound or salt of claim 1 wherein $R_3$ is -Ar'—Y—$R_4$ wherein Ar' is phenylene, Y is selected from the group consisting of —C(O)—, —C(O)—$N(R_8)$—, —$N(R_8)$—C(O)—, —$N(R_8)$—$S(O)_2$—, and —$N(R_8)$—C(O)—$N(R_8)$— wherein $R_8$ is selected from hydrogen and methyl; and $R_4$ is selected from the group consisting of $C_{1-6}$ alkyl, morpholin-4-yl, phenyl, and phenyl substituted by a substituent selected from the group consisting of alkyl, alkoxy, halogen, hydroxy, and hydroxyalkyl.

11. The compound of claim 1 selected from the group consisting of 2-hydroxymethyl-1-(2-methylpropyl)-7-phenyl-1H-imidazo[4,5-c]quinolin-4-amine, 2-(2-hydroxyethyl)-1-(2-methylpropyl)-7-phenyl-1H-imidazo[4,5-c]quinolin-4-amine, 1-(4-amino-2-hydroxymethyl-7-phenyl-1H-imidazo[4,5-c]quinolin-1-yl)-2-methylpropan-2-ol, and 1-[4-amino-2-(2-hydroxyethyl)-7-phenyl-1H-imidazo[4,5-c]quinolin-1-yl]-2-methylpropan-2-ol, or a pharmaceutically acceptable salt thereof.

12. The compound of claim 1 selected from the group consisting of N-[4-(4-amino-2-hydroxymethyl-7-phenyl-1H-imidazo[4,5-c]quinolin-1-yl)butyl]methanesulfonamide and N-{4-[4-amino-2-(2-hydroxyethyl)-7-phenyl-1H-imidazo[4,5-c]quinolin-1-yl]butyl]}methanesulfonamide, or a pharmaceutically acceptable salt thereof.

13. The compound of claim 1 selected from the group consisting of 2-hydroxymethyl-1-(2-methylpropyl)-7-(pyridin-3-yl)-1H-imidazo[4,5-c]quinolin-4-amine, 2-(2-hydroxyethyl)-1-(2-methylpropyl)-7-(pyridin-3-yl)-1H-imidazo[4,5-c]quinolin-4-amine, 1-[4-amino-2-hydroxymethyl-7-(pyridin-3-yl)-1H-imidazo[4,5-c]quinolin-1-yl]-2-methylpropan-2-ol, and 1-[4-amino-2-(2-hydroxyethyl)-7-(pyridin-3-yl)-1H-imidazo[4,5-c]quinolin-1-yl]-2-methylpropan-2-ol, or a pharmaceutically acceptable salt thereof.

14. The compound of claim 1 selected from the group consisting of N-{4-[4-amino-2-hydroxymethyl-7-(pyridin-3-yl)-1H-imidazo[4,5-c]quinolin-1-yl]butyl]}methanesulfonamide and N-{4-[4-amino-2-(2-hydroxyethyl)-7-(pyridin-3-yl)-1H-imidazo[4,5-c]quinolin-1-yl]butyl]}methanesulfonamide, or a pharmaceutically acceptable salt thereof.

15. A pharmaceutical composition comprising a therapeutically effective amount of a compound or salt of claim 1 and a pharmaceutically acceptable carrier.

16. A method of preferentially inducing the biosynthesis of IFN-α in an animal comprising administering an effective amount of a compound or salt of claim 1 to the animal.

17. A method of treating a viral disease in an animal in need thereof comprising administering a therapeutically effective amount of a compound or salt of claim 1 to the animal.

18. A method of treating a neoplastic disease in an animal in need thereof comprising administering a therapeutically effective amount of a compound or salt of claim 1 to the animal.

* * * * *